(12) United States Patent  
Boutillette et al.

(10) Patent No.: US 9,078,660 B2  
(45) Date of Patent: Jul. 14, 2015

(54) DEVICES AND METHODS FOR DELIVERING AN ENDOCARDIAL DEVICE

(75) Inventors: Michael P. Boutillette, San Francisco, CA (US); James R. Kermode, Los Altos, CA (US); Miles D. Alexander, Sunnyvale, CA (US); Alexander Khairkhahan, Palo Alto, CA (US); Serjan D. Nikolic, Los Altos, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 927 days.

(21) Appl. No.: 12/893,832

(22) Filed: Sep. 29, 2010

(65) Prior Publication Data

US 2011/0087066 A1    Apr. 14, 2011

Related U.S. Application Data

(63) Continuation-in-part of application No. 11/860,438, filed on Sep. 24, 2007, now Pat. No. 7,897,086, which is a continuation-in-part of application No. 10/913,608, filed on Aug. 5, 2004, now abandoned, (Continued)

(51) Int. Cl.
    *A61N 1/362*    (2006.01)
    *A61B 17/12*    (2006.01)
    *A61B 17/00*    (2006.01)

(52) U.S. Cl.
    CPC ..... *A61B 17/12122* (2013.01); *A61B 17/12022* (2013.01); *A61B 17/12172* (2013.01);
    (Continued)

(58) Field of Classification Search
    CPC .............. A61B 17/12022; A61B 17/12122; A61B 17/12172; A61B 2017/12054; A61B 2017/12095; A61F 2/2418

USPC ............. 623/2.17, 3.16–3.2; 600/16, 37
See application file for complete search history.

(56) References Cited

U.S. PATENT DOCUMENTS 3,874,388 A    4/1975 King et al.
4,007,743 A    2/1977 Blake
(Continued)

FOREIGN PATENT DOCUMENTS

EP    1474032 A2    11/2004
EP    2068768 A     6/2009
(Continued)

OTHER PUBLICATIONS

Khairkhahan Alexander; U.S. Appl. No. 13/129,961 entitled "Devices and methods for delivering an endocardial device," filed Jul. 14, 2011.

(Continued)

*Primary Examiner* — Tammie K Heller
(74) *Attorney, Agent, or Firm* — Shay Glenn LLP

(57) ABSTRACT

Systems for partitioning a ventricle of a heart include a partitioning device or implant, and an applicator for inserting, repositioning and/or removing the partitioning device. The implant may support the ventricle wall and may reduce the volume of the ventricle. The delivery system for delivering and deploying a partitioning device into a ventricle may include a catheter having a distal coupling element for coupling to a partitioning device in a collapsed configuration; the catheter may also have an expansion member for applying force to the partitioning device to fully expand it into a deployed configuration and to secure or seal it against the ventricle wall.

38 Claims, 26 Drawing Sheets

Related U.S. Application Data application No. 12/893,832, which is a continuation-in-part of application No. 12/509,289, filed on Jul. 24, 2009, now Pat. No. 8,398,537, which is a continuation of application No. 11/151,164, filed on Jun. 10, 2005, now Pat. No. 7,582,051.

(60) Provisional application No. 61/246,920, filed on Sep. 29, 2009.

(52) U.S. Cl.
CPC ............... *A61B2017/00243* (2013.01); *A61B 2017/00867* (2013.01); *A61B 2017/12054* (2013.01); *A61B 2017/12095* (2013.01)

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,636,720 B2 | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 * | 2/2007 | Leasure .................... 600/16 |
| 7,175,660 B2 | 2/2007 | Cartledge et al. |
| 7,320,665 B2 | 1/2008 | Vijay |
| 7,399,271 B2 | 7/2008 | Sharkey et al. |
| 7,485,088 B2 | 2/2009 | Murphy et al. |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |

(56) References Cited

U.S. PATENT DOCUMENTS

| | | |
|---|---|---|
| 7,762,943 B2 | 7/2010 | Khairkhahan |
| 7,824,325 B2 | 11/2010 | Dubi |
| 7,862,500 B2 | 1/2011 | Sharkey et al. |
| 7,993,258 B2 | 8/2011 | Felt et al. |
| 8,382,653 B2 | 2/2013 | Dubi et al. |
| 8,500,622 B2 | 8/2013 | Lipperman et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0078671 A1 | 4/2003 | Lesniak et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | Van Tassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0116692 A1 | 6/2006 | Ward |
| 2006/0136043 A1 | 6/2006 | Cully et al. |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0264980 A1 | 11/2006 | Khairkhahan et al. |
| 2006/0276684 A1 | 12/2006 | Speziali |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0071298 A1 | 3/2008 | Khairkhahan et al. |
| 2008/0228205 A1 | 9/2008 | Sharkey et al. |
| 2008/0293996 A1 | 11/2008 | Evans et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0187063 A1 | 7/2009 | Khairkhahan |
| 2009/0254195 A1 | 10/2009 | Khairkhahan et al. |
| 2009/0287040 A1 | 11/2009 | Khairkhahan et al. |
| 2010/0030256 A1 | 2/2010 | Dubrul et al. |
| 2010/0048987 A1 | 2/2010 | Khairkhahan et al. |
| 2010/0121132 A1 | 5/2010 | Nikolic et al. |
| 2010/0262168 A1 | 10/2010 | Khairkhahan et al. |
| 2010/0274227 A1 | 10/2010 | Khairkhahan et al. |
| 2011/0092761 A1 | 4/2011 | Almog et al. |
| 2011/0178362 A1 | 7/2011 | Evans et al. |
| 2012/0041257 A1 | 2/2012 | Stankus et al. |
| 2012/0259356 A1 | 10/2012 | Khairkhahan |
| 2013/0090677 A1 | 4/2013 | Evans et al. |
| 2013/0165735 A1 | 6/2013 | Khairkhahan et al. |
| 2013/0270735 A1 | 10/2013 | Alexander |
| 2013/0274595 A1 | 10/2013 | Kermode et al. |
| 2014/0180271 A1 | 6/2014 | Johnson et al. |
| 2014/0296624 A1 | 10/2014 | Kermode et al. |
| 2014/0343356 A1 | 11/2014 | Nikolic et al. |

FOREIGN PATENT DOCUMENTS

| | | | |
|---|---|---|---|
| EP | 2344070 A | | 7/2011 |
| EP | 2244661 B1 | | 3/2012 |
| EP | 2082690 B1 | | 6/2012 |
| JP | H08257031 A | | 10/1996 |
| JP | 2001520910 | | 11/2001 |
| JP | 2003512128 A | | 4/2003 |
| JP | 2003512129 A | | 4/2003 |
| JP | 2005324019 | | 11/2005 |
| JP | 2008508955 | | 3/2008 |
| WO | WO 96/37859 A1 | | 11/1996 |
| WO | WO 98/03213 A1 | | 1/1998 |
| WO | WO 00/27292 | | 5/2000 |
| WO | WO 00/42919 A1 | | 7/2000 |
| WO | WO 00/50639 A2 | | 8/2000 |
| WO | WO 01/30266 | | 5/2001 |
| WO | WO 01/78625 | | 10/2001 |
| WO | WO 02/30335 | | 4/2002 |
| WO | WO 02/45710 A1 | | 6/2002 |
| WO | WO 02/071977 A2 | | 9/2002 |
| WO | WO 02/087481 A1 | | 11/2002 |
| WO | WO 03/007778 | | 1/2003 |
| WO | WO 03/043507 A2 | | 5/2003 |
| WO | WO 03/073961 A1 | | 9/2003 |
| WO | WO 03/090716 A1 | | 11/2003 |
| WO | WO 03/099300 A1 | | 12/2003 |
| WO | WO 03/099320 A1 | | 12/2003 |
| WO | WO 03/103538 A1 | | 12/2003 |
| WO | WO 03/103743 A2 | | 12/2003 |
| WO | WO 2004/012629 | | 2/2004 |
| WO | WO 2004/019866 A2 | | 3/2004 |
| WO | WO 2004/066805 A2 | | 8/2004 |
| WO | WO 2004/100803 A1 | | 11/2004 |
| WO | WO 2005/007031 | | 1/2005 |
| WO | WO 2005/007873 A2 | | 1/2005 |
| WO | WO 2005/041745 A2 | | 5/2005 |
| WO | WO 2005/091860 A2 | | 10/2005 |
| WO | WO 2005/102181 A1 | | 11/2005 |

(56) References Cited

FOREIGN PATENT DOCUMENTS

| WO | WO 2006/033107 A2 | 3/2006 |
|---|---|---|
| WO | WO 2006/055683 A2 | 5/2006 |
| WO | WO 2007/016349 A2 | 2/2007 |
| WO | WO 2007/092354 | 8/2007 |
| WO | WO 2007/143560 A2 | 12/2007 |
| WO | WO 2011/011641 A2 | 1/2011 |

OTHER PUBLICATIONS

Boersma et al.; Early thrombolytic treatment in acute myocardial infarction: reappraisal of the golden hour; Lancet: vol. 348; pp. 771-775; 1996.
Sharkey et al.; Left ventricular apex occluder. Description of a a ventricular partitioning device; EuroInterv.; 2(1); pp. 125-127; May 2006.
U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).
Khairkhahan, Alexander; U.S. Appl. No. 13/954,221 entitled "Retrievable Cardiac Devices," filed Jul. 30, 2013.
Nikolic et al.; U.S. Appl. No. 13/973,868 entitled "Therapeutic Methods and Devices Following Myocardial Infarction," filed Aug. 22, 2013.
AGA Medical Corporation. www.amplatzer.com/products. "The Muscular VSD Occluder" and "The Septal Occluder" device description. Accessed Apr. 3, 2002.
Artrip et al.; Left ventricular volume reduction surgery for heart failure: A physiologic perspective; J Thorac Cardiovasc Surg; vol. 122; No. 4; pp. 775-782; 2001.
Di Mattia, et al. Surgical treatment of left ventricular post-infarction aneurysm with endoventriculoplasty: late clinical and functioal results. European Journal of Cardio-thoracic Surgery. 1999; 15:413-418.
Dor, et al. Ventricular remodeling in coronary artery disease. Current Opinion in Cardiology. 1997; 12:533-537.
Dor, V. The treatment of refractory ischemic ventricular tachycardia by endoventricular patch plasty reconstruction of the left ventricle. Seminars in Thoracic and Cardiovascular Surgery. 1997; 9(2): 146-155.
Dor. Surgery for left ventricular aneurysm. Current Opinion in Cardiology. 1990; 5: 773-780.
Gore Medical. www.goremedical.com. "Helex Septal Occluder" product description. Accessed Apr. 3, 2002.
Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.
Katsumata, et al. An objective appraisal of partial left ventriculectomy for heart failure. Journal of Congestive Heart Failure and Circulator Support. 1999; 1(2): 97-106.
Kawata, et al. Systolic and Diastolic Function after Patch Reconstruction of Left Ventricular Aneurysms. Ann. Thorac. Surg. 1995; 59:403-407.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.
Kermode et al.; U.S. Appl. No. 12/912,632 entitled "Ventrical volume reduction," filed Oct. 26, 2010.
Anand et al.; Isolated myocyte contractile function is normal in postinfarct remodeled rat heart with systolic dysfunction; Circulation ; 96(11); pp. 3974-3984; Dec. 1997.
Dang et al.; Akinetic myocardial infarcts must contain contracting myocytes: finite-element model study; Am J Physiol Heart Circ Physiol ; 288; pp. H1844-H1850; Apr. 2005.
Dang et al.; Effect of ventricular size and patch stiffness in surgical anterior ventricular restoration: a finite element model study; Ann Thorac Surg; 79; pp. 185-193; Jan. 2005.
Grossman et al.; Wall stress and patterns of hypertrophy in the human left ventricle; J Clin Invest; 56; pp. 56-64; Jul. 1975.
Guccione et al.; Finite element stress analysis of left ventricular mechanics in the beating dog heart; J Biomech; 28; pp. 1167-1177; Oct. 1995.
Guccione et al.; Mechanics of active contraction in cardiac muscle: Part II—Cylindrical models of the systolic left ventricle; J Biomech Eng; 115; pp. 82-90; Feb. 1993.
Gutberlet et al.; Myocardial viability assessment in patients with highly impaired left ventricular function: comparison of delayed enhancement, dobutamine stress MRI, end-diastolic wall thickness, and TI201-SPECT with functional recovery after revascularization; Eur Radiol; 15; pp. 872-880; May 2005.
Huisman et al.; Measurement of left ventricular wall stress; Cardiovascular Research; 14; pp. 142-153; Mar. 1980.
Jackson et al.; Extension of borderzone myocardium in postinfarction dilated cardiomyopathy; J Am Coll Cardiol; 40(6); 1160-7; and discussion; pp. 1168-1171; Sep. 2002.
Jones et al.; Coronary Bypass Surgery with or without Surgical Ventricular Reconstruction; N Engl J Med; 360; pp. 1705-1717; Apr. 2009.
Nikolic et al.; Percutaneous implantation of an intraventricular device for the treatment of heart failure: experimental results and proof of concept; J Card Fail; 15(9); pp. 790-797; Nov. 2009.
Priola et al.; Functional characteristics of the left ventricular inflow and outflow tracts; Circ Res; 17; pp. 123-129; Aug. 1965.
Sagic et al.; Percutaneous implantation of the left ventricular partitioning device for chronic heart failure: a pilot study with 1-year follow-up. Eur J Heart Fail; 12; pp. 600-606; Apr. 2010.
Sun et al.; A computationally efficient formal optimization of regional myocardial contractility in a sheep with left ventricular aneurysm (author manuscript, 21 pgs.); J Biomech Eng; 131; 111001; Nov. 2009.
Walker et al; Magnetic resonance imaging-based finite element stress analysis after linear repair of left ventricular aneurysm (author manuscript, 17 pgs.); J Thorac Cardiovasc Surg; 135; pp. 1094-1102 e1-2; May 2008.
Walker et al; MRI-based finite-element analysis of left ventricular aneurysm; Am J Physiol Heart Circ Physiol; 289; pp. H692-H700; Aug. 2005.
Walmsley; Anatomy of left ventricular outflow tract; British Heart Journal; 41; pp. 263-267; Mar. 1979.

* cited by examiner

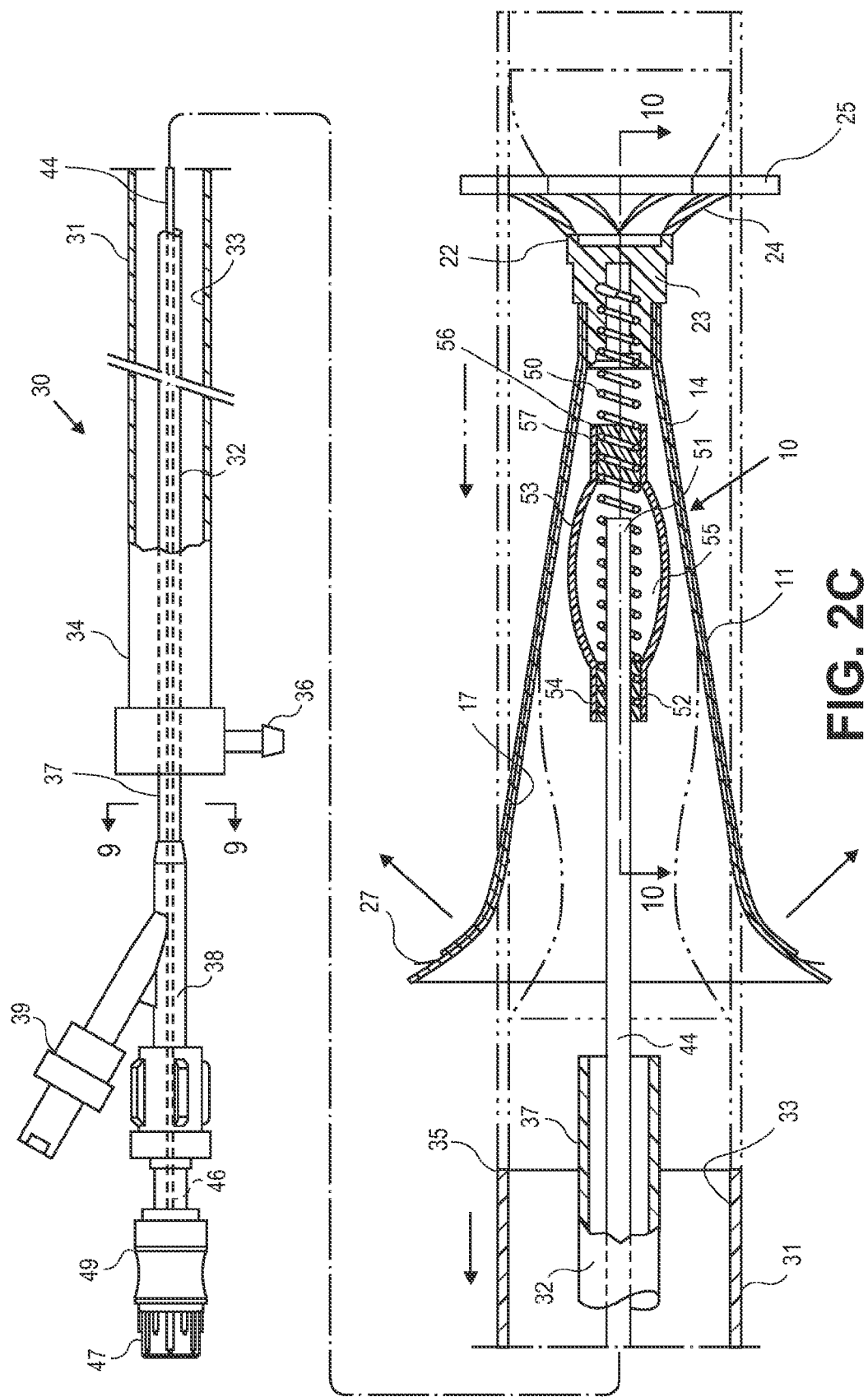

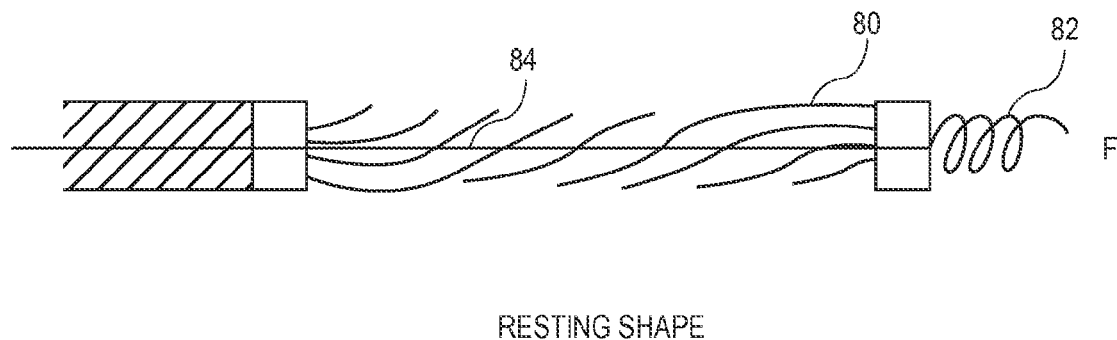
RESTING SHAPE
FIG. 20
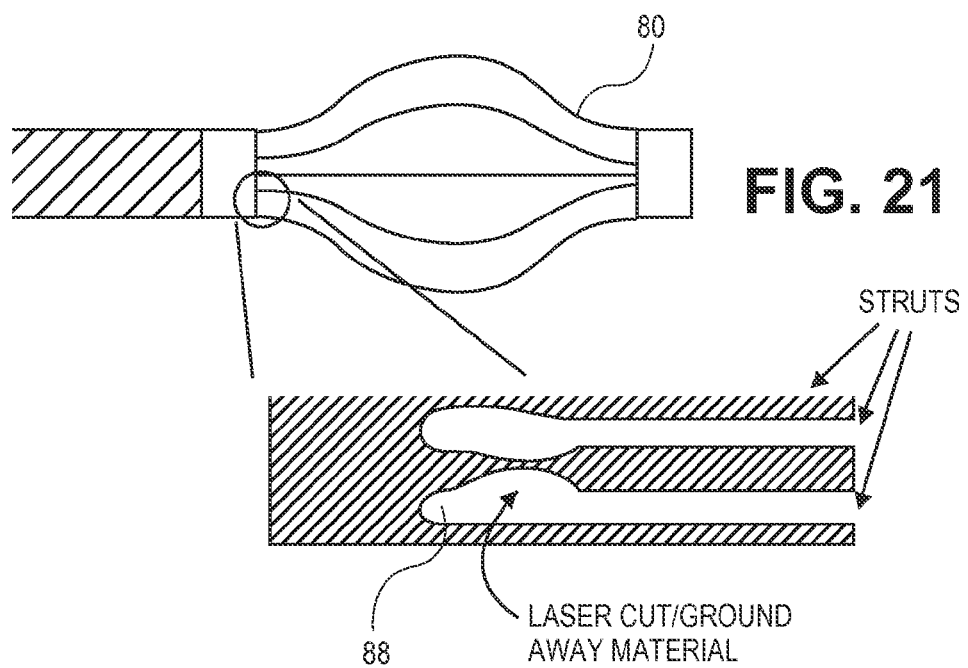
FIG. 21
FIG. 21A

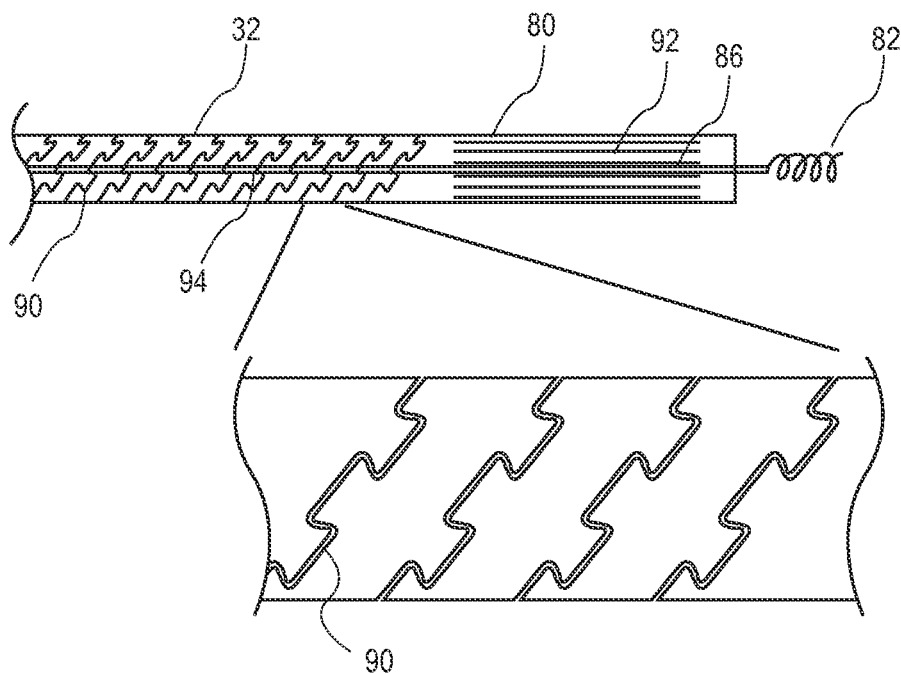
FIG. 22
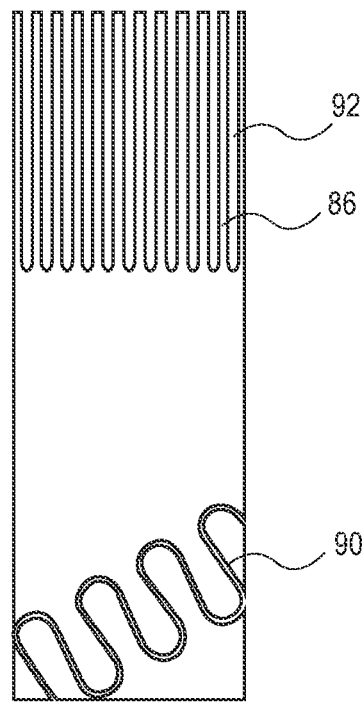 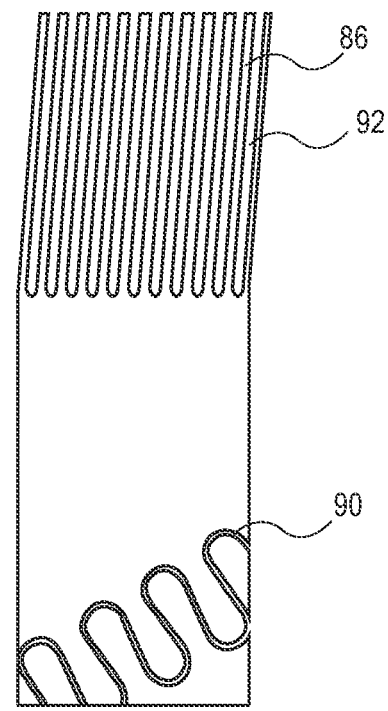
FIG. 23A     FIG. 23B

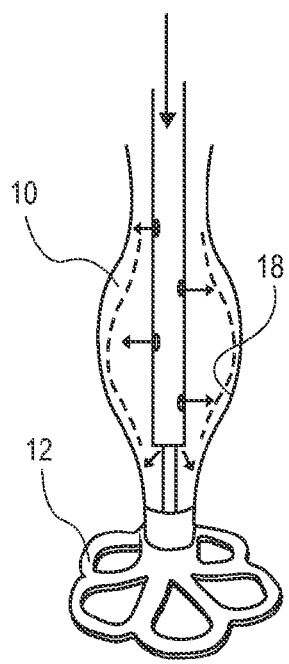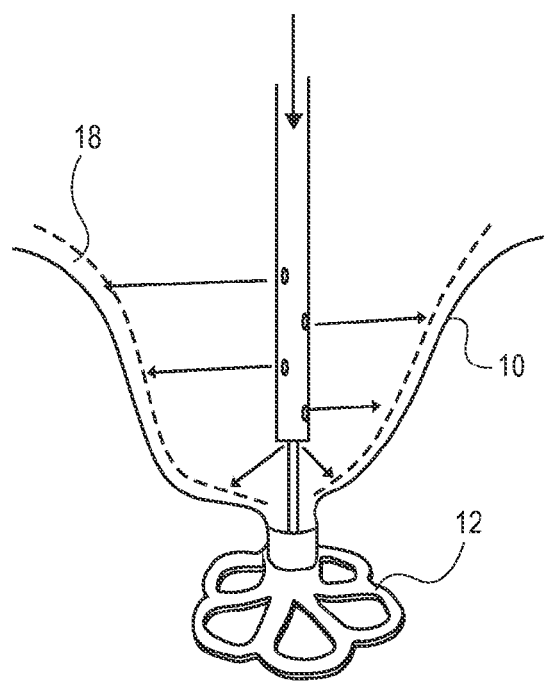
FIG. 27A
FIG. 27B

DEVICES AND METHODS FOR DELIVERING AN ENDOCARDIAL DEVICE

CROSS REFERENCE TO RELATED APPLICATIONS

This patent application claims priority as a continuation-in-part of U.S. patent application Ser. No. 11/860,438, filed on Sep. 24, 2007, now U.S. Pat. No. 7,897,086, which is a continuation-in-part of U.S. patent application Ser. No. 10/913,608, filed on Aug. 5, 2004, US Patent Application Publication No. 2006-0030881-A1 (now abandoned). This patent application also claims priority as a continuation-in-part of U.S. patent application Ser. No. 12/509,289, filed on Jul. 24, 2009, now U.S. Pat. No. 8,398,537, which is a continuation-in-part of U.S. patent application Ser. No. 11/151,164, filed on Jun. 10, 2005, now U.S. Pat. No. 7,582,051. This patent application also claims priority to U.S. provisional patent application Ser. No. 61/246,920, filed Sep. 29, 2009. Each of these patent applications is herein incorporated by reference in their entirety.

The devices and methods described herein may be applied to many of the devices and systems described in any of the references listed below. In particular, these references generally describe devices, systems, and methods for improving cardiac function and to ventricular partitioning devices in particular. Thus, the following patents/patent applications are herein incorporated by reference in their entirety: U.S. patent application Ser. No. 09/635,511, filed on Aug. 9, 2000 (titled "DEVICE AND METHOD FOR TREATMENT OF HOLLOW ORGANS"); U.S. patent application Ser. No. 10/212,032, filed on Aug. 1, 2002 (titled "METHOD FOR IMPROVING CARDIAC FUNCTION"); U.S. patent application Ser. No. 10/212,033, filed on Aug. 1, 2002 (titled "DEVICE FOR IMPROVING CARDIAC FUNCTION"); U.S. patent application Ser. No. 10/302,269, filed on Nov. 22, 2002 (titled "DEVICE WITH A POROUS MEMBRANE FOR IMPROVING CARDIAC FUNCTION"); U.S. patent application Ser. No. 10/302,272, filed on Nov. 22, 2002 (titled "METHOD OF IMPROVING CARDIAC FUNCTION USING A POROUS MEMBRANE"); U.S. patent application Ser. No. 10/382,962, filed on Mar. 6, 2003 (titled "METHOD FOR IMPROVING CARDIAC FUNCTION"); U.S. patent application Ser. No. 10/436,959, filed on May 12, 2003 (titled "SYSTEM FOR IMPROVING CARDIAC FUNCTION"); U.S. patent application Ser. No. 10/754,182, filed on Jan. 9, 2004 (titled "VENTRICULAR PARTITIONING DEVICE"); U.S. patent application Ser. No. 10/791,916, filed on Mar. 3, 2004 (titled "INFLATABLE VENTRICULAR PARTITIONING DEVICE"); U.S. patent application Ser. No. 10/913,608, filed on Aug. 5, 2004 (titled "VENTRICULAR PARTITIONING DEVICE"); U.S. patent application Ser. No. 11/151,156, filed on Jun. 10, 2005 (titled "MULTIPLE PARTITIONING DEVICES FOR HEART TREATMENT"); U.S. patent application Ser. No. 11/151,164, filed on Jun. 10, 2005 (titled "PERIPHERAL SEAL FOR A VENTRICULAR PARTITIONING DEVICE"); U.S. patent application Ser. No. 11/199,633, filed on Aug. 9, 2005 (titled "METHOD FOR TREATING MYOCARDIAL RUPTURE"); U.S. patent application Ser. No. 11/640,469, filed on Dec. 14, 2006 (titled "CARDIAC DEVICE AND METHODS OF USE THEREOF"); U.S. patent application Ser. No. 11/800,998, filed on May 7, 2007 (titled "SYSTEM FOR IMPROVING CARDIAC FUNCTION"); U.S. patent application Ser. No. 11/801,075, filed on May 7, 2007 (titled "SYSTEM FOR IMPROVING CARDIAC FUNCTION"); U.S. patent application Ser. No. 11/860,438, filed on Sep. 24, 2007 (titled "LAMINAR VENTRICULAR PARTITIONING DEVICE"); U.S. patent application Ser. No. 12/125,015, filed on May 21, 2008 (titled "VENTRICULAR PARTITIONING DEVICE"); U.S. patent application Ser. No. 12/129,443, filed on May 29, 2008 (titled "THERAPEUTIC METHODS AND DEVICES FOLLOWING MYOCARDIAL INFARCTION"); U.S. patent application Ser. No. 12/181,282, filed on Jul. 28, 2008 (titled "INFLATABLE VENTRICULAR PARTITIONING DEVICE"); U.S. patent application Ser. No. 12/198,010, filed on Aug. 25, 2008 (titled "RETRIEVABLE DEVICES FOR IMPROVING CARDIAC FUNCTION"); U.S. patent application Ser. No. 12/198,022, filed on Aug. 25, 2008 (titled "RETRIEVABLE CARDIAC DEVICES"); and U.S. patent application Ser. No. 12/268,346, filed on Nov. 10, 2008 (titled "SYSTEM FOR IMPROVING CARDIAC FUNCTION").

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The present invention relates generally to medical/surgical devices and methods pertaining to treating heart disease, particularly heart failure. More specifically, the present invention relates to devices and methods for delivering a partitioning device to a patient's ventricle.

BACKGROUND OF THE INVENTION

Described herein are systems, methods and devices for improving cardiac function, and may relate generally to treating heart disease, particularly heart failure, and more specifically, to systems, methods, and devices for delivering a partitioning device to a patient's ventricle.

Heart failure annually leads to millions of hospital visits internationally. Heart failure (including congestive heart failure) is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischemia may, for example, cause a portion of a myocardium of the heart to lose its ability to contract. Prolonged ischaemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, diastolic pressures increase, which stretches the ventricular chamber prior to contraction and greatly increases the pressure in the heart. In response, the heart tissue reforms to accommodate the chronically increased filling pressures, further increasing the work that the now compromised myocardium must perform.

Drug therapy typically treats the symptoms of the disease and may slow the progression of the disease, but it cannot cure the disease. One of the only permanent treatments for heart failure is heart transplantation, but heart transplant procedures are very risky, extremely invasive and expensive and are performed on only a small percentage of patients. Many patient's do not qualify for heart transplant for failure to meet any one of a number of qualifying criteria, and, furthermore, there are not enough hearts available for transplant to meet the needs of HF patients who do qualify.

Substantial effort has been made to find alternative treatments for heart failure. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to the most severe class of patients and, accordingly, is not an option for most patients facing ineffective drug treatment. Finally, if the procedure fails, emergency heart transplant is the only presently available option.

Ventricular partitioning devices offer a solution for treating heart failure. These devices generally function to partition a patient's ventricle into a productive region and a non-productive region. For such devices to function properly, they are positioned in a specific location within the patient's heart chamber. Delivery of a partitioning device may be made complicated by the anatomy of a patient and by aspects or characteristics of the delivery device or partitioning device itself. Thus, it would be beneficial to provide devices, systems and methods for delivering and deploying a partitioning device in a patient's ventricle.

The systems for reducing ventricular volume described herein may include delivery systems and devices for delivering partitioning devices. A partitioning device, or implant, may be an umbrella-shaped partitioning implant, and may be included as part of the system for reducing ventricular volume. The delivery systems may include a guide catheter for guiding the implant to the ventricle, positioning it within the implant, expanding the implant to partition the ventricle, and release the implant from the catheter, deploying it in position.

SUMMARY OF THE INVENTION

Described herein are systems, apparatus and methods for partitioning a heart. The systems may include a partitioning device or implant, applicators for inserting, repositioning and/or removing them, and methods of positioning, deploying and removing them. The implants described herein are cardiac implants that may be inserted into a chamber of a patient's heart, particularly the left ventricle. The implant may support the heart wall, or in some variations the implant is a ventricular partitioning device for partitioning the ventricle into productive and non-productive regions, and/or for reducing the volume of the ventricle.

For example, the devices and systems described herein may include a delivery system (or insertion tools, such as a catheter and sheath/guide tool) and a ventricular partitioning device including a plurality of ribs, configured to expand within the patient's ventricle. The delivery system may include one or more catheters (e.g., a guide catheter, delivery catheter, etc.). In some embodiments, the systems described herein include an elongate catheter having an expandable member at the distal end of the guide catheter configured to expand the ventricular partitioning device and a coupling element at the distal tip of the guide catheter configured to couple the ventricular partitioning device to the guide catheter.

Described herein are systems for reducing the volume of a patent's ventricle. The system may include a delivery device (or delivery system) as described in detail herein, as well as a ventricular partitioning device. Any combination of any of the delivery systems and partitioning devices described herein may be used.

For example, a system for delivering a ventricular partitioning device into a patient's ventricle and deploying the partitioning device to reduce the effective volume of the ventricle by expanding the partitioning device from a collapsed delivery configuration into an expanded deployed configuration, may include: an elongate guide catheter having a proximal end and a distal end; an expansion member near the distal end of the guide catheter and configured to expand a plurality of struts of the partitioning device by applying pressure to the collapsed partitioning device to open the partitioning device and secure it in the ventricle; and a coupling element distal to the expansion member and configured to deployably secure to a hub of the partitioning device to retain the expansion member at least partially surrounded by the collapsed partitioning device prior to deployment.

The system may further comprise an expansion control for expanding the expansion member to apply pressure and expand the ventricular partitioning device. Any appropriate expansion control may be used, including an inflation lumen connected to the expansion member, a pullwire for pulling on the expansion member to expand it, or the like. The expansion control may also include a manipulatable control, such as a button, knob, slider, or dial on the proximal end of the elongate guide catheter for controlling expansion of the expansion member.

The system may also include a deployment control for releasing the coupling element from the hub of the ventricular partitioning device. Any appropriate deployment control may be used, including (but not limited to) a torque shaft connected to the coupling element for unscrewing the coupling element from the ventricular partitioning device, a pullwire connected to the coupling element for pulling a hitch pin to release the ventricular partitioning device, or the like.

The deployment control and the expansion control may be separately activated. In some variations, the expansion control may be repeatedly activated to expand/contract the partitioning device.

As mentioned, any of the systems described herein may also include a ventricular partitioning device. For example, a system may include a ventricular partitioning device comprising an umbrella-like structure having a plurality of struts joined at a central hub.

The catheter (e.g., guide catheter) may include any appropriate expansion member. For example, the expansion member may be a hydraulic expansion member comprising a plurality of openings for releasing pressurized fluid to apply pressure to expand the ventricular partitioning device, an inflatable expansion member (e.g., a balloon), or a mechanical expander. A mechanical expansion member may include a plurality of struts joined at their proximal and distal ends and configured to expand outwards when the proximal and distal ends are brought closer together.

The catheter may also include any appropriate coupling element, including mechanical coupling members such as helical screws, hitch pins, or the like.

In some variations of the system, the guide catheter further comprises a proximal handle having a one-handed activation release.

The systems described herein may also include a steering mechanism that bends the distal end region of the guide catheter. The steering mechanism may include tendons or pull wires that pull one or more sides of the catheter to bend the catheter for steering. In some variations, described in greater detail below, the catheter is adapted to be steered by bending selectively in one or more directions. In some variations, the catheter includes hinge-points or cut-out regions that allow for column strength (allowing pushing/pulling of the catheter axially), while making the catheter flexible in one or more directions. The catheter may also be formed of multiple layers; for example, a guide catheter may include an outer catheter formed of a metal or other appropriate material providing column strength and having a lumen in which an inner catheter resides. The inner catheter may also include one or more lumen (e.g., an inflation lumen, a perfusion lumen, etc.). The catheter may also include a pullwire and/or a torque wire.

In one variation, a system for delivering a ventricular partitioning device into a patient's ventricle and deploying the partitioning device to reduce the effective volume of the ventricle by expanding the partitioning device from a collapsed delivery configuration into an expanded deployed configuration may include: an elongate guide catheter having a proximal end and a distal end; an expansion member near the distal end of the guide catheter and configured to expand the partitioning device by applying pressure to open the collapsed partitioning device and secure it in the ventricle; a coupling element distal to the expansion member and configured to deployably secure to a hub of the partitioning device to retain the expansion member at least partially surrounded by the collapsed partitioning device prior to deployment; an expansion control at the proximal end of the elongate guide catheter for expanding the expansion member to apply pressure and expand the partitioning device; and a deployment control for releasing the partitioning device from the guide catheter by separating the coupling element from the hub of the partitioning device.

As mentioned above, any of the systems described herein, including the system for delivery a partitioning device into a patient's ventricle and deploying the partitioning device, may include any of the features described. For example, the system may include an expansion control comprising an inflation lumen connected to the expansion member a pullwire for pulling on the expansion member to expand it, etc. The system may also include controls such as a button, knob, slider, or dial on the proximal end of the elongate guide catheter for controlling expansion of the expansion member.

Also described herein are delivery systems for delivering an umbrella-shaped ventricular partitioning device into a patient's ventricle and mechanically deploying the partitioning device to reduce the effective volume of the ventricle by expanding the partitioning device from a collapsed configuration into an expanded configuration. These systems may comprise: an elongate guide catheter having a proximal end and a distal end; a mechanical expander near the distal end of the guide catheter having a plurality of arms configured to extend outwards when operated to apply pressure to the partitioning device to open the partitioning device; and a coupling element distal to the expansion member and configured to deployably secure to a central hub of the partitioning device and to retain the expansion member at least partially surrounded by the collapsed partitioning device prior to deployment.

Also described herein are delivery system for delivering an umbrella-shaped ventricular partitioning device into a patient's ventricle and deploying the partitioning device to reduce the effective volume of the ventricle by expanding the partitioning device from a collapsed configuration into an expanded configuration, the system comprising: an elongate guide catheter having a proximal end and a distal end; a mechanical expander near the distal end of the guide catheter comprising a plurality of arms joined at their proximal and distal ends and configured to expand outwards when the proximal and distal ends are brought closer together, the mechanical expander configured to apply pressure the partitioning device to open the partitioning device and secure it in the ventricle; and a coupling element distal to the expansion member and configured to deployably secure to a hub of the partitioning device and to retain the expansion member at least partially surrounded by the collapsed partitioning device prior to deployment.

In some variations, a delivery system for delivering an umbrella-shaped ventricular partitioning device into a patient's ventricle and deploying the partitioning device to reduce the effective volume of the ventricle by expanding the partitioning device from a collapsed configuration into an expanded configuration, includes: an elongate guide catheter having a proximal end and a distal end; an inflatable expander near the distal end of the guide catheter configured to extend outwards when inflated to apply pressure to open the partitioning device and to secure the partitioning device in the ventricle; a distal nose spacer distal to the inflatable expander on the guide catheter and configured to space the inflatable expander proximally from a central hub region of the partitioning device; a taper region between the distal nose spacer and the inflatable expander; and a coupling element distal to the expansion member and configured to deployably secure to the central hub of the partitioning device and to retain the expansion member at least partially surrounded by the partitioning device prior to deployment.

Also described herein are delivery systems for delivering an umbrella-shaped ventricular partitioning device into a patient's ventricle and mechanically deploying the partitioning device to reduce the effective volume of the ventricle by expanding the partitioning device from a collapsed configuration into an expanded configuration, the system comprising: an elongate guide catheter having a proximal end and a distal end; a pressure expander near the distal end of the guide catheter comprising a plurality of openings from a fluid source line extending along the length of the elongate catheter, the plurality of openings positioned near the distal end region of the elongate guide catheter and configured to release fluid and apply pressure to the proximal end region of the partitioning device to expand the partitioning device; and a coupling element distal to the expansion member and configured to deployably secure to a central hub of the partitioning device and to retain the expansion member at least partially surrounded by the partitioning device prior to deployment.

Also described are systems for reducing the effective volume of the ventricle by securing a ventricular partitioning device within the ventricle, the system comprising: an umbrella-shaped ventricular partitioning device having a central hub, a plurality of struts, and a membrane, wherein the partitioning device has a collapsed delivery configuration and an expanded deployed configuration; and a delivery system. The delivery system may include: an elongate guide catheter having a proximal end and a distal end; a mechanical expander near the distal end of the guide catheter comprising a plurality of arms joined configured to extend outwards to expand the ventricular partitioning device by applying pressure against the struts to open the ventricular partitioning device; a expansion pullwire coupled to the mechanical expander; and a coupling element distal to the expansion member and configured to deployably secure to the central hub of the partitioning device and to retain the expansion member at least partially surrounded by the collapsed partitioning device prior to deployment.

Methods of partitioning a ventricle, and method of reducing ventricular volume, are also described. The methods described herein may generally include the steps of advancing the distal end of a delivery or guide catheter into the patient's ventricle, positioning the distal end of the guide catheter within the ventricle, expanding a ventricular partitioning device within the ventricle to partition the ventricle, and deploying the ventricular partitioning device from the distal end of the guide catheter. The device may be secured, and/or sealed, to the ventricle wall(s).

For example, described herein are methods of reducing ventricular volume to treat heart disease, the method comprising: positioning an umbrella-shaped, expandable partitioning device having a reinforced membrane in a contracted configuration near the apex of a patients' ventricle using an elongate guide catheter to which the partitioning device is releasably coupled; expanding an expansion member near the distal end of the guide catheter to apply pressure to the proximal end region of the contracted partitioning device to expand the partitioning device; and releasing a coupling element distal to the expansion member on the guide catheter to deploy the partitioning device.

In some variations, the method also includes a step of securing the periphery of the partitioning device to the ventricle wall. For example, the guide catheter may be configured to expand to drive open the partitioning device and secure it to the wall of the ventricle. The method may also include the step of sealing the periphery of the partitioning device to the ventricle wall.

In some variations, the method also includes percutaneously guiding the partitioning device on the end of the guide catheter into the ventricle. For example, the method may include advancing the partitioning device into the ventricle through an inner lumen of a delivery catheter.

The method may include the step of expanding the expansion member by expanding an inflatable expansion member near the distal end of the guide catheter. The step of expanding the expansion member may comprise expanding a plurality of arms joined at their proximal and distal ends by expand bringing the proximal and distal ends closer together. In some variations, the step of expanding the expansion member comprises expelling fluid from a plurality of openings positioned near the distal end region of the guide catheter to apply pressure to the proximal end region of the partitioning device to expand the partitioning device.

The step of releasing a partitioning device from the catheter (guide catheter that has guided and positioned the device) may be preformed after the device has been positioned in the appropriate region of the ventricle, typically the apical region. This guidance may be performed under visualization, such as fluoroscopy. Once positioned, the device may be deployed and released from the catheter by disengaging the coupling member. For example, the coupling element may be released by rotating a torque shaft that rotates to withdraw a helical coil screw (e.g., the screw and torque shaft may form part of the coupling element) from a hub of the partitioning device.

BRIEF DESCRIPTION OF THE DRAWINGS

FIG. 2C shows another variation of a system for reducing ventricular volume include a partitioning device.

FIGS. 13A-21A illustrate various embodiments of the delivery system wherein the expandable member is a mechanical expansion member.

FIGS. 22-24 illustrate various embodiments of the delivery system wherein the frame and the delivery catheter are formed from a single tube.

FIGS. 27A-27B illustrate various embodiments of the delivery system wherein the expandable member is a hydraulic system.

DETAILED DESCRIPTION OF THE INVENTION

Devices, systems and methods for reducing ventricular volume by partitioning the ventricle may be used to treat cardiac or circulatory disorders. In general, the devices and systems described herein include partitioning devices for partitioning the ventricle into productive and non-productive regions. The partitioning device described herein may also be referred to as a ventricular volume reduction devices or implants. Also described herein are delivery devices for delivering and/or deploying the ventricular volume reduction implants. The delivery devices may also be referred to as catheters, or more specifically as guide catheters. As used herein, a guide catheter may be used for delivering and/or deploying a partitioning device into a patient's ventricle. Any of the systems described herein may include both a guide catheter and a partitioning device/volume reduction device. A partitioning device may be pre-loaded onto the guide catheter. The following description is not intended to limit the invention to the illustrated embodiments, but rather to enable any person skilled in the art to make and use this invention.

A ventricular partitioning device typically includes a plurality of ribs, configured to expand within the patient's ventricle, and a membrane that may be reinforced by the ribs. The ribs may also be referred to as struts. In some variations, the partitioning device/volume reduction device may be an umbrella-type device or implant, having a hub to which the ribs or struts extend; the device may have a collapsed delivery configuration (resembling a collapsed umbrella) and an expanded delivery configuration. Although the partitioning device may be pre-biased in the expanded configuration, the delivery device (guide catheter) may include an expansion element to help fully expand, position, and secure the implant in the ventricle. For example, in some variations the implant includes a plurality of struts or ribs formed of a memory material such as Nitinol that self-expands at least partially into the deployed configuration. When deploying with a guide catheter, the guide catheter may force expansion of the partitioning device and insertion into the wall of the ventricle.

In some examples, the systems described herein include an elongate guide catheter having an expandable member at the distal end of the guide catheter configured to expand the ventricular partitioning device and a coupling element at the distal tip of the guide catheter configured to couple the ventricular partitioning device to the guide catheter. In general, the methods described herein include the steps of advancing the distal end of a guide catheter into the patient's ventricle, positioning the distal end of the guide catheter within the ventricle, deploying the ventricular partitioning device from the distal end of the guide catheter, and expanding a ventricular partitioning device within the ventricle to partition the ventricle.

Figure 1:
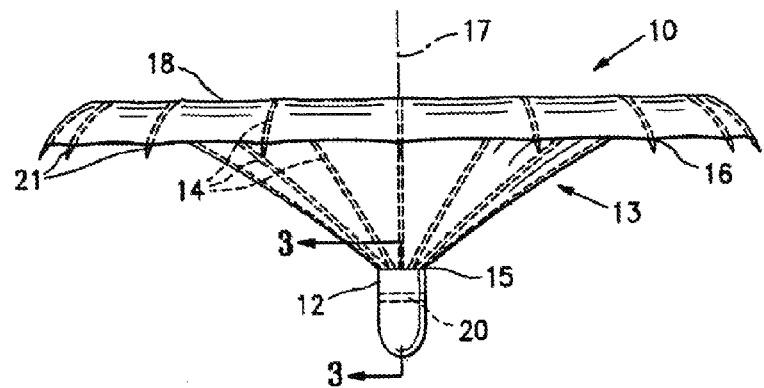
FIG. 1 illustrates a partitioning device embodying features of the invention in an expanded configuration.

FIG. 1 illustrates one variation of a partitioning component 10 which embodies features of the invention and which includes a partitioning membrane 11 (not shown), a hub 12, preferably centrally located on the partitioning device, and a radially expandable reinforcing frame 13 formed of a plurality of ribs 14. Preferably, the partitioning membrane 11 is secured to the proximal or pressure side of the frame 13 as shown in FIG. 1. The ribs 14 have distal ends 15 which are secured to the hub 12 and free proximal ends 16 which are configured to curve or flare away from a center line axis 17. Radial expansion of the free proximal ends 16 unfurls the membrane 11 secured to the frame 13 so that the membrane presents a relatively smooth, pressure receiving surface 18 which defines in part the productive portion of the patient's partitioned heart chamber. The ribs 14 are pre-shaped so that when not constrained other than by the membrane 11 secured thereto (as shown in FIG. 1), the free proximal ends 16 thereof expand to a desired angular displacement away from a center line axis 17. In some variations the implant includes a foot or feet at the distal end of the hub 12. In some variations the edge of the membrane may be configured to seal against the ventricle wall, e.g., by including a sealing surface or reinforcement.

Figure 2A:
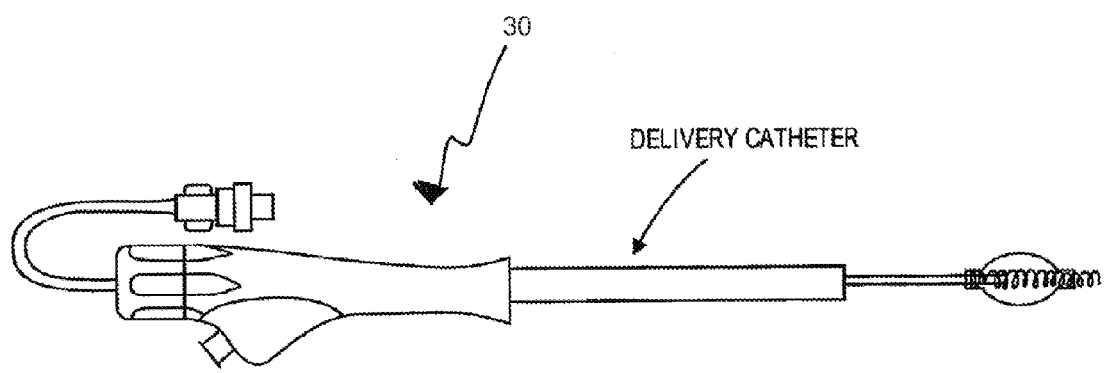
FIGS. 2A and 2B illustrates a system for reducing ventricular volume including a delivery system (guide catheter) and the partitioning device shown in FIG. 1.
Figure 2B:
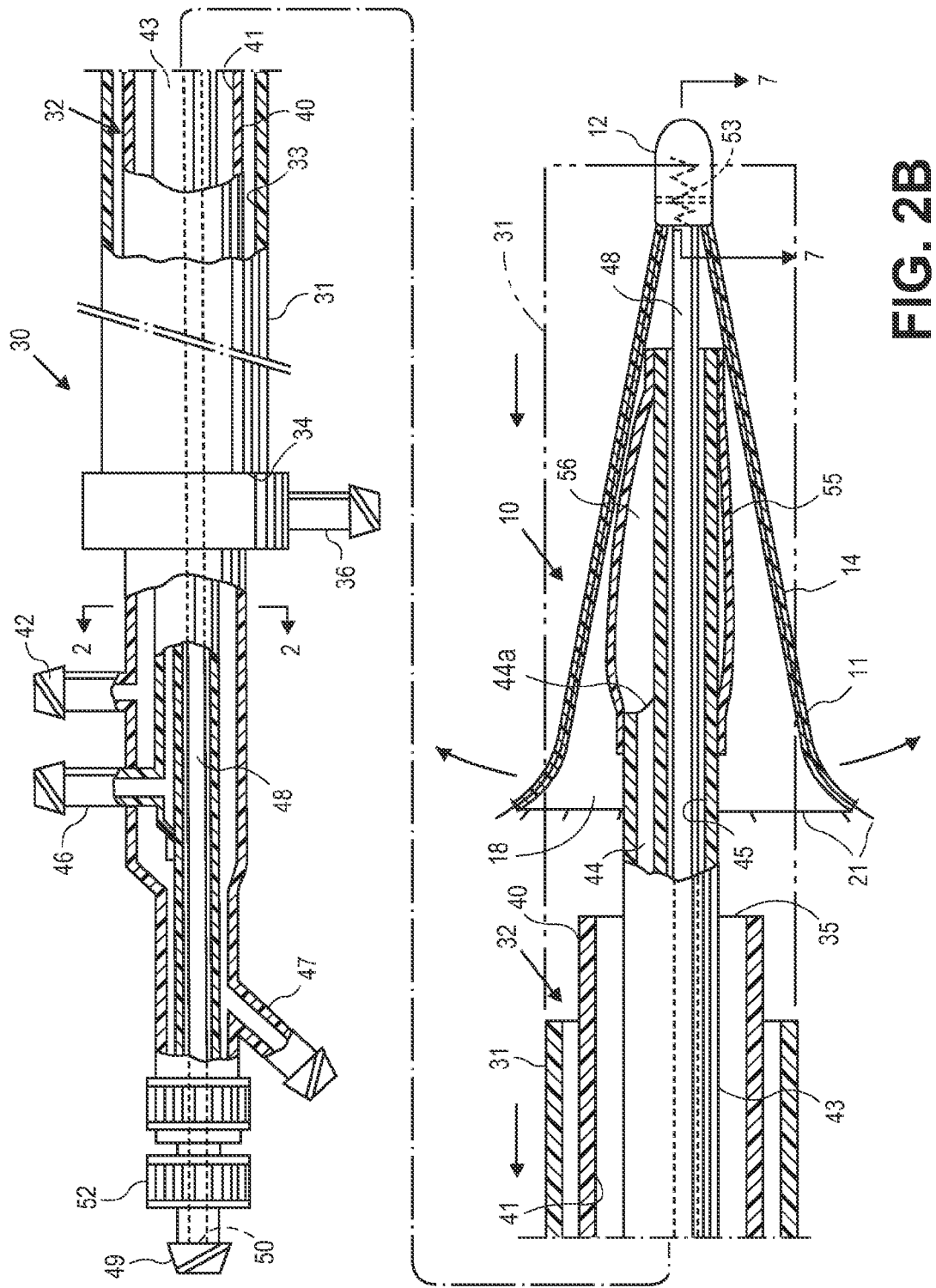

FIG. 2A illustrates one variations of a system 30 for delivering a partitioning device 10 (as illustrated in FIG. 1) into a patient's heart chamber and deploying the partitioning device 10 to partition the heart chamber as illustrated in FIGS. 3A-3E. This delivery system typically includes a guide catheter. FIG. 2B shows a schematic view of the delivery system including a guide catheter and delivery catheter shown in FIG. 2A.

The guide catheter has an inner lumen 33 extending between the proximal end 34 and distal end 35. A hemostatic valve (not shown) may be provided at the proximal end 34 of the guide catheter 31. A flush port 36 on the proximal end 34 of guide catheter 31 is in fluid communication with the inner lumen 33.

The delivery catheter 32 has an outer shaft 40 with an inner lumen 41 and a proximal injection port 42, an inner shaft 43 disposed within the inner lumen 41 with a first lumen 44 and a second lumen 45. Balloon inflation port 46 is in fluid communication with the first lumen 44 and flush port 47 is in fluid communication with the second lumen 45. Torque shaft 48 is rotatably disposed within the second lumen 44 of the inner shaft 43 and has an injection port 49 provided at its proximal end 50 in fluid communication with the inner lumen 51 of the torque shaft. The torque shaft 48 in this example is formed at least in part of a hypotube formed of suitable material such as superelastic Nitinol or stainless steel. A torque knob 52 is secured to the proximal end 50 of torque shaft 48 distal to the injection port 49. A helical coil screw 53 is secured to the distal end 54 of the torque shaft 48 and rotation of the torque knob 52 on the proximal end 50 of the torque shaft 48 rotates the screw 53 on the distal end 54 of torque shaft 48 to facilitate deployment of a partitioning device 10. In this example, the screw and torque shaft form a coupling element on the guide catheter that may releasably secure a partitioning device so that it may be delivered. An inflatable balloon 55 is sealingly secured to the distal end of the inner shaft 43 and has an interior 56 in fluid communication with the first lumen 44. The inflatable expansion member is but one variation of an expansion member that may form part of the guide catheter. Inflation fluid may be delivered to the interior 56 through port 44a in the portion of the inner shaft 43 extending through the balloon 55. Inflation of the balloon 55 by inflation fluid through port 57 facilitates securing the partitioning component 10.

Figure 3A:
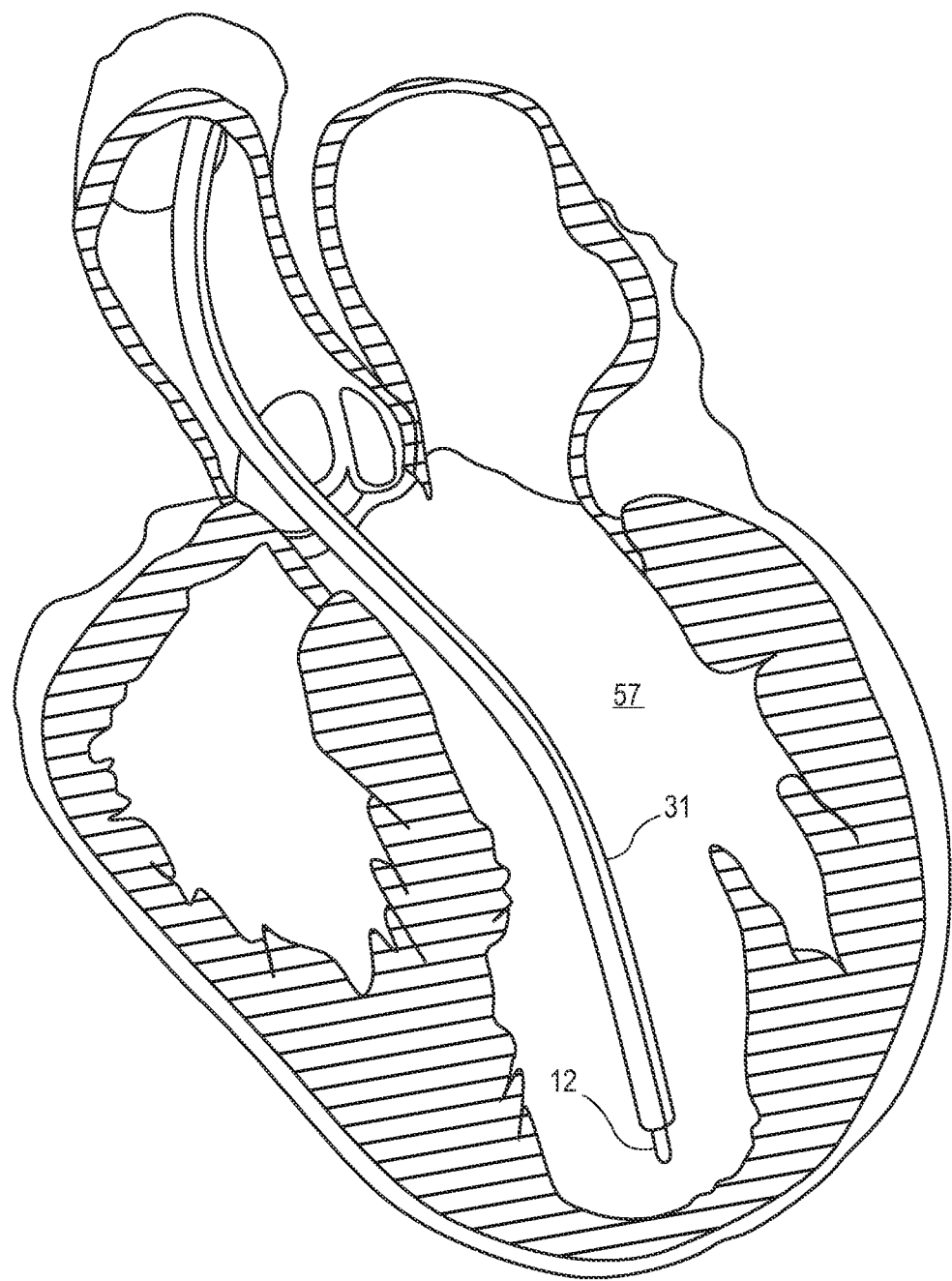
FIGS. 3A-3E are schematic views of a patient's left ventricular chamber illustrating the deployment of the partitioning device shown in FIG. 1 with the delivery system shown in FIG. 2 to partition the heart chamber into a primary productive portion and a secondary, non-productive portion.

As mentioned, to deliver the partitioning component 10, it is secured to the distal end of the delivery catheter 32 by means of a coupling mechanism, such as a helical coil screw. The partitioning component 10 is collapsed to a first, delivery configuration which has small enough transverse dimensions to be slidably advanced through the guide catheter 31 (FIG. 3A). In some embodiments, the guide catheter 31 has been previously percutaneously introduced and advanced through the patient's vasculature, such as the femoral artery, in a conventional manner to the desired heart chamber. The delivery catheter 32 (FIG. 3C) with the partitioning component 10 attached is advanced through the inner lumen of the guide catheter 31 until the partitioning component 10 is ready for deployment from the distal end of the guide catheter 31 into the patient's heart chamber 57 to be partitioned.

Figure 3B:
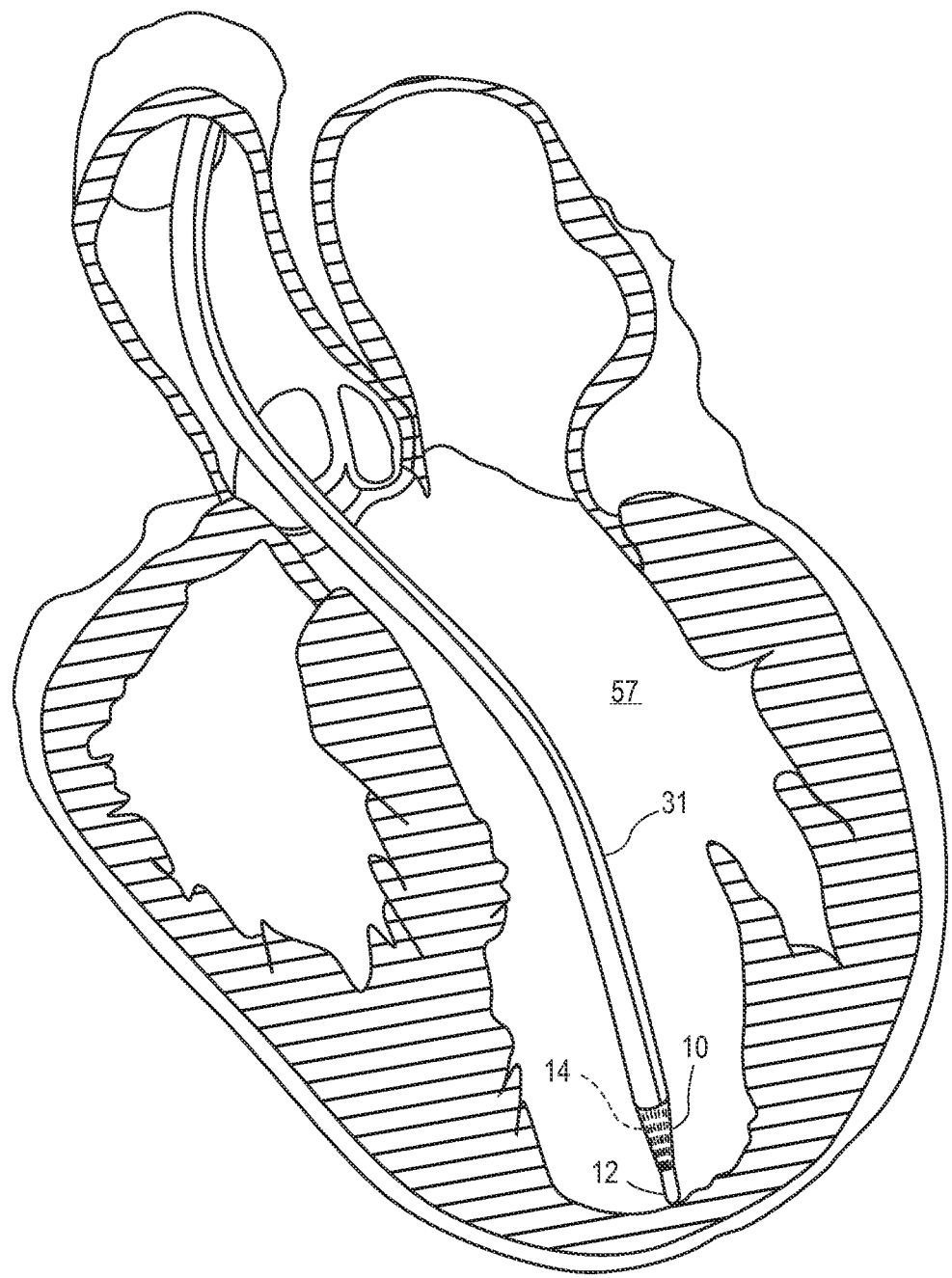
Figure 3C:
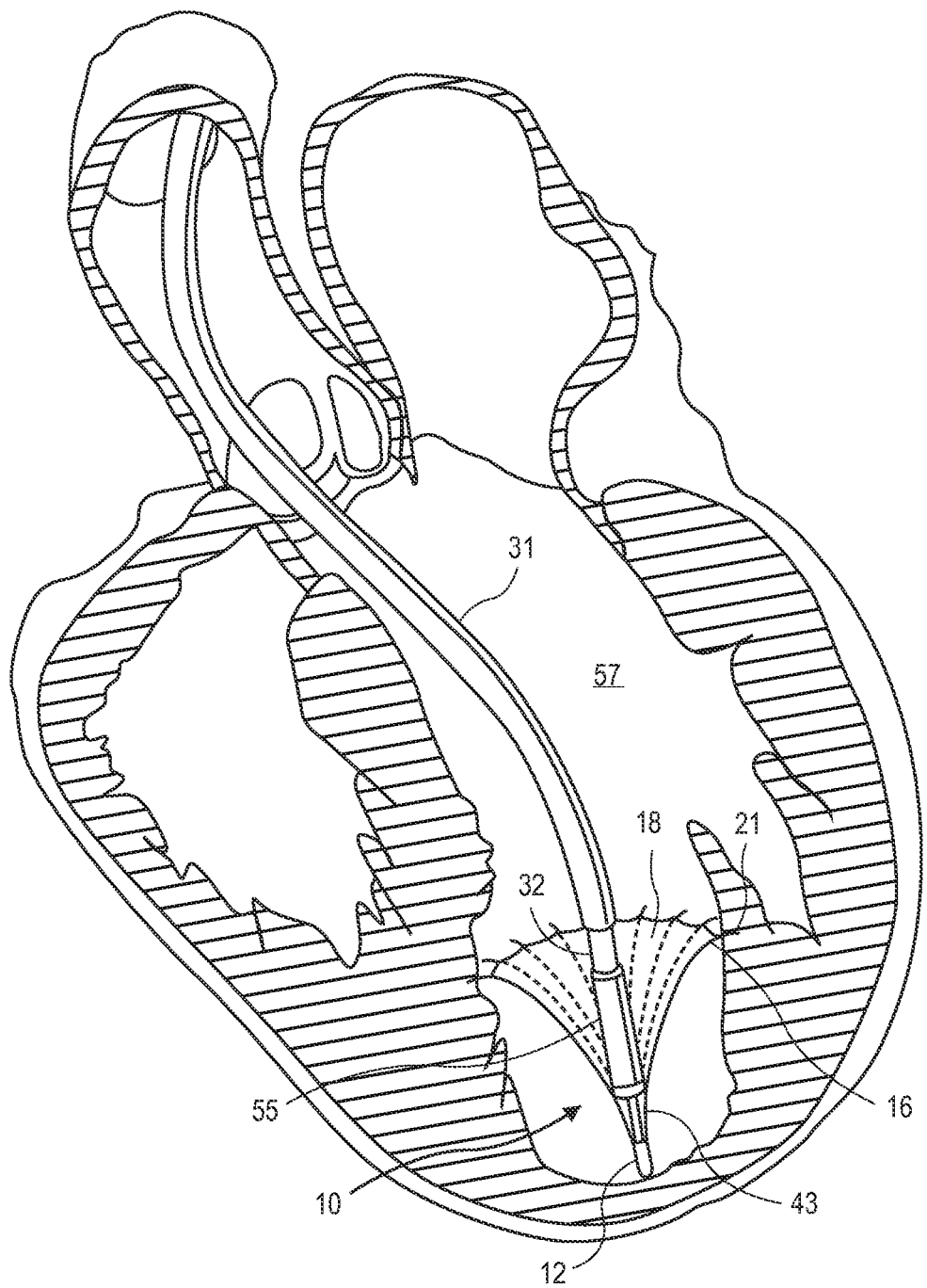

The partitioning component 10 mounted on the coupling element (screw 53, as shown) may be urged partially out of the inner lumen of the guide catheter 31 until the hub 12 engages the heart wall as shown in FIG. 3B with the free proximal ends 16 of the ribs 14 in a contracted configuration within the guide catheter. The guiding catheter 31 is withdrawn while the delivery catheter 32 is held in place until the proximal ends 16 of the ribs 14 exit the distal end 35 (not shown) of the guiding catheter. The free proximal ends 16 of ribs 14 expand outwardly to press the sharp proximal tips 21 of the ribs 14 against and preferably into the tissue lining the heart chamber. This is shown in FIG. 3C.

Figure 3D:
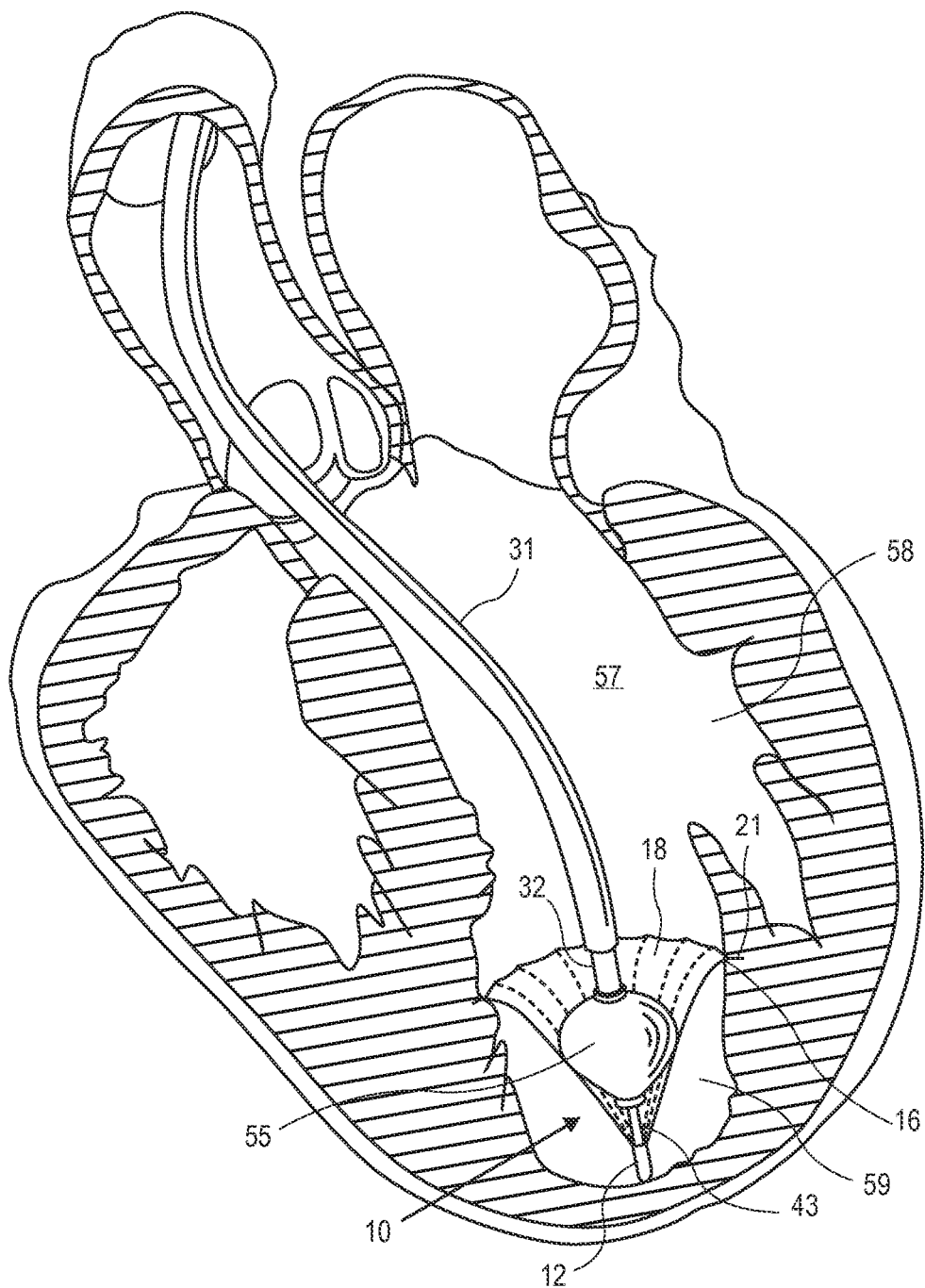

With the partitioning component deployed within the heart chamber and preferably partially secured therein, inflation fluid may be introduced through the inflation port 46 into first lumen 44 of inner shaft 43 of the delivery catheter 32 where it is directed through port 44a into the balloon interior 56 to inflate the balloon. This is shown in FIG. 3D. The inflated balloon presses against the pressure receiving surface 18 of the partitioning component 10 to ensure that the sharp proximal tips 21 are pressed well into the tissue lining the heart chamber.

Figure 3E:
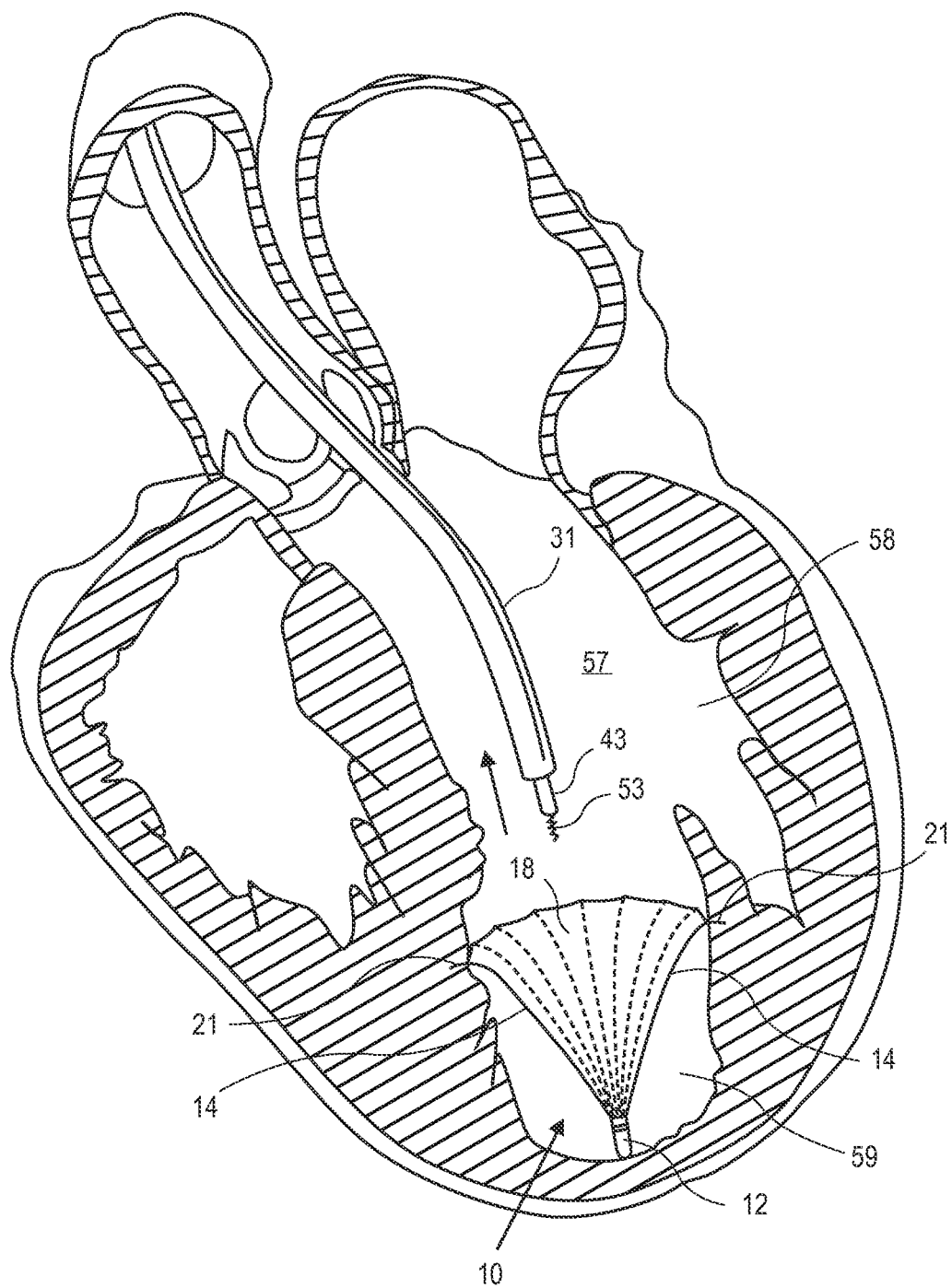

With the partitioning device 10 properly positioned within the heart chamber, the knob 52 on the torque shaft 48 is rotated counter-clockwise to disengage the helical coil screw 53 of the delivery catheter 32 from the hub 12. This is illustrated in FIG. 3E. The counter-clockwise rotation of the torque shaft 48 rotates the helical coil screw 53 which rides on the connector bar 20 secured within the hub 12. Once the helical coil screw 53 disengages the connector bar 20, the delivery system 30, including the guide catheter 31 and the delivery catheter 32, may then be removed from the patient.

The proximal end of the guide catheter 31 may be provided with a flush port 36 to inject therapeutic or diagnostic fluids through the inner lumen 33. Similarly, the proximal end of the delivery catheter 32 may be provided with a flush port 42 in communication with inner lumen 41 for essentially the same purpose. An inflation port 46 is provided on the proximal portion of the delivery catheter for delivery of inflation fluid through the first inner lumen 44 to the interior 56 of the balloon 55. Flush port 47 is provided in fluid communication with the second inner lumen 45 of the inner shaft 43. An injection port 49 may be provided on the proximal end of the torque shaft 48 in fluid communication with the inner lumen 51 of the torque shaft for delivery of a variety of fluids.

The partitioning component 10 in this example partitions the patient's heart chamber 57 into a main productive or operational portion 58 and a secondary, essentially non-productive portion 59, thereby reducing the ventricular volume. The operational portion 58 is much smaller than the original ventricular chamber 57 and provides for an improved ejection fraction. The partitioning increases the ejection fraction and provides an improvement in blood flow. Over time, the non-productive portion 59 fills first with thrombus and subsequently with cellular growth. Bio-resorbable fillers such as polylactic acid, polyglycolic acid, polycaprolactone and copolymers and blends may be employed to initially fill the non-productive portion 59. Fillers may be suitably supplied in a suitable solvent such as DMSO. Other materials which accelerate tissue growth or thrombus may be deployed in the non-productive portion 59.

FIG. 2C illustrates another variation of a system 30 for delivering a partitioning device 10. Although the embodiments of the delivery systems show in various embodiments may be different, common features are labeled the same.

The delivery system 30 includes a guide catheter 31 and a delivery catheter 32. As in the variation shown in FIG. 2B, the guide catheter 31 has an inner lumen 33 extending between the proximal end 34 and distal end 35. A hemostatic valve (not shown) may be provided at the proximal end 34 of the guide catheter 31 to seal about the outer shaft 37 of the delivery catheter 32. A flush port 36 on the proximal end 34 of guide catheter 31 is in fluid communication with the inner lumen 33.

Figure 4:
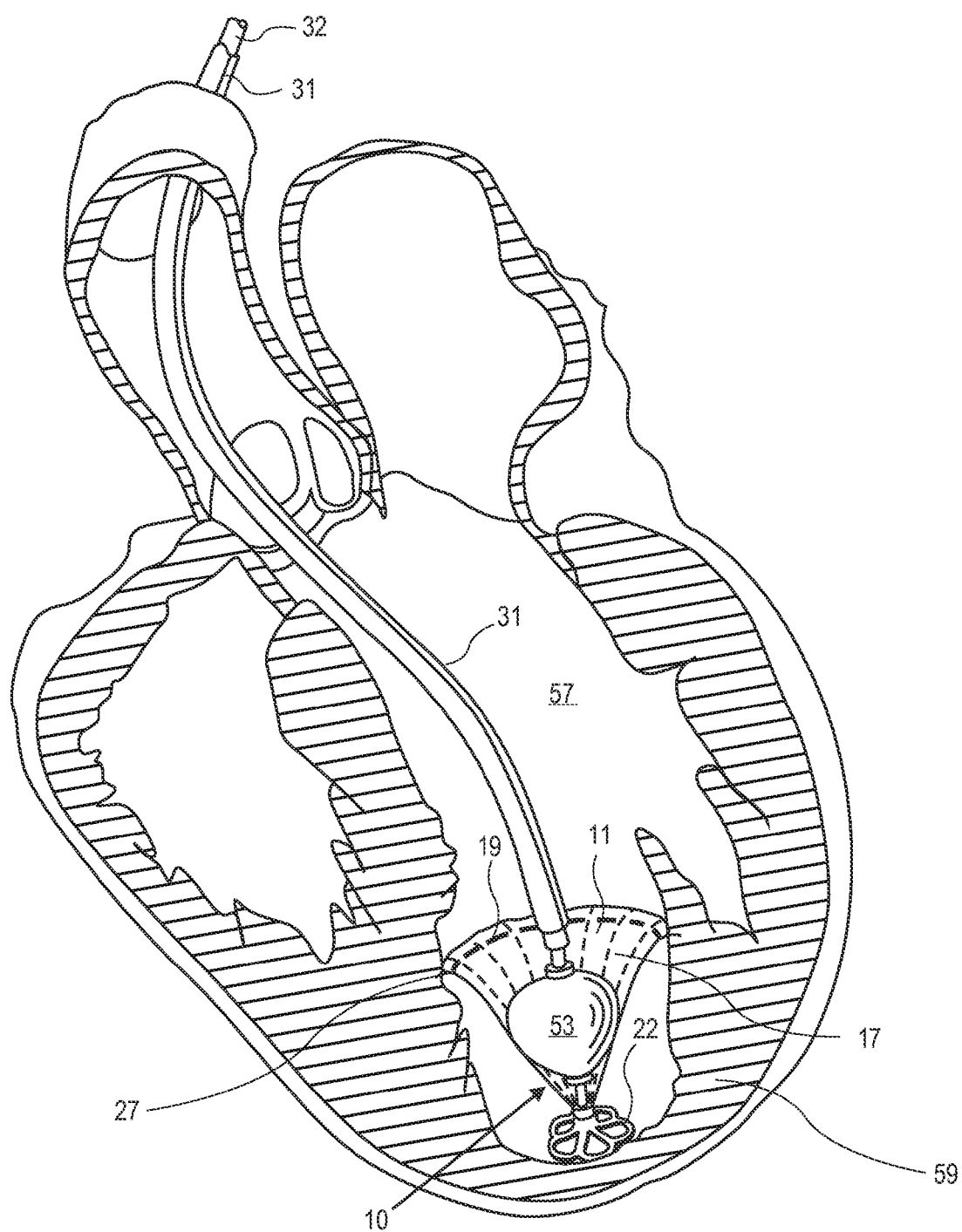
FIG. 4 illustrates deployment of the variation shown in FIG. 2C.

The delivery catheter 32 has an outer shaft 37 with an adapter 38 on the proximal end thereof having a proximal injection port 39 which is in fluid communication with the interior of the shaft 37. The outer shaft 37 may have an inner shaft which is disposed within the interior thereof and is secured to the inner surface of the outer shaft by webs which extend along a substantial length of the inner shaft. The injection port may be in fluid communication with the passageways between the inner and outer shafts and defined in part by the webs. A torque shaft, which is preferably formed of hypotubing (e.g. formed of stainless steel or superelastic NiTi), may be disposed within the inner lumen of the inner shaft and has a proximal end 46 secured within the adapter 38. Balloon inflation port 47 is in fluid communication with the inner lumen of the torque shaft 44. Torque shaft 44 is rotatably disposed within the inner lumen 45 of the inner shaft 41 and is secured to rotating knob 49. A helical coil screw 50 is secured to the distal end 51 of the torque shaft 44 and rotation of the torque knob 49 on the proximal end 46 of the torque shaft 44 rotates the screw 51 to facilitate deployment of a partitioning device 10. The proximal end 52 of inflatable balloon 53 is sealingly secured by adhesive 54) about the torque shaft 44 proximal to the distal end 51 of the torque shaft. The balloon 53 has an interior 55 in fluid communication with the inner lumen 48 of the torque shaft 44. Inflation fluid may be delivered to the balloon interior 55 through port 47 which is in fluid communication with the inner lumen 48 of the torque shaft 44. The distal end 56 of the balloon 53 is sealingly secured by adhesive 57 to the helical screw 50. The proximal and distal ends 52 and 56 of the balloon 53 are blocked by the adhesive masses 54 and 57 to prevent the loss of inflation fluid delivered to the interior 55 of the balloon 53. Delivery of inflation fluid through a fluid discharge port 58 in the distal end 51 of the torque shaft 44 inflates the balloon 53 which in turn applies pressure to the proximal surface of the partitioning device 10 to facilitate securing the partitioning component 10 to the wall 59 of heart chamber. The device may be inserted substantially as shown in FIGS. 3A-3E described above. FIG. 4 illustrates deployment of the partitioning device and delivery catheter similar illustrated in FIG. 2C; this figure resembles FIG. 3D, above.

In FIG. 3E, with the partitioning device 10 properly positioned within the heart chamber 57, the knob 49 on the torque shaft 44 (as shown in FIG. 2C) is rotated counter-clockwise to disengage the helical coil screw 50 of the delivery catheter 32 from the stem 23 secured within hub 12. The counter-clockwise rotation of the torque shaft 44 rotates the helical coil screw 50 which rides on the connector bar 26 secured within the hub 12. Once the helical coil screw 50 disengages the connector bar 26, the delivery system 30, including the guide catheter 31 and the delivery catheter 32, may then be removed from the patient.

The proximal end 34 of the guide catheter 31 is provided with a flush port 36 to inject fluids such as therapeutic, diagnostic or other fluids through the inner lumen 33 during the procedure. Similarly, the proximal injection port 39 of adapter 38 is in communication with passageways 43 if the delivery catheter 32 for essentially the same purpose.

In this example, the implant also includes a sealing element, strand 19, which may be used to help stiffen the edge of the membrane so that it may lie against the ventricle wall and form a seal against the wall. The strand may also be used to help retrieve the device.

Figure 5:
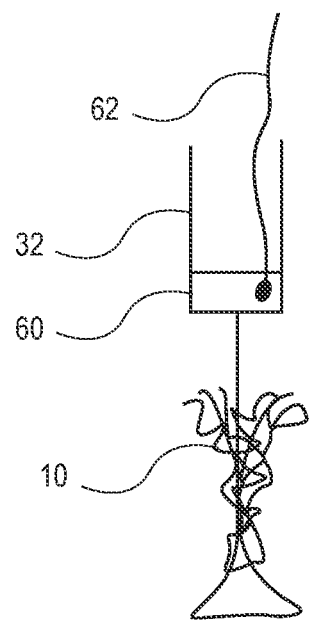
FIGS. 5-8 illustrate various embodiments of the delivery system configured to maintain the position of the partitioning device while the guide catheter is withdrawn.

In some embodiments, as the guide catheter 31 is withdrawn, it begins to bend as it is withdrawn through the vascular anatomy of the patient, through the aortic arch, for example. In some instances, this bend may drive the distal tip of the delivery catheter, and therefore the partitioning device, out of position. For example, the guide catheter may drive the device towards the center of the heart, i.e. towards the ventricular septum. In some instances, it may be preferred that the delivery catheter and/or partitioning device are not moved or repositioned by the guide catheter as it is withdrawn. This may be accomplished in one of several embodiments. In a first embodiment, as shown in FIG. 5, a ring 60 is added to the distal end of the delivery catheter 32. A wire 62 may be coupled to the ring. The wire may be disposed along the length of the delivery and/or guide catheter, and may be configured to maintain the position of the distal end of the delivery catheter as the guide catheter is retracted into the vascular anatomy. For example, in some variations the wire is a rigidifying wire (or other element) that locks or holds the shape of the delivery catheter. In some variations, the wire is a pull wire. By pulling on or tensioning the pull wire, as shown in FIG. 5, the pull wire pulls on the ring 60, bending the delivery catheter. This may prevent the ring and distal end of the delivery catheter, and therefore the partitioning device, from moving out of position. The pull wire, for example, may be used to pull the delivery catheter and partitioning device toward the apex of the heart, rather than towards the ventricular septum. In this embodiment, the guide catheter may be flexible such that the pull wire may effectively steer the delivery catheter as the guide catheter is withdrawn.

Figure 6:
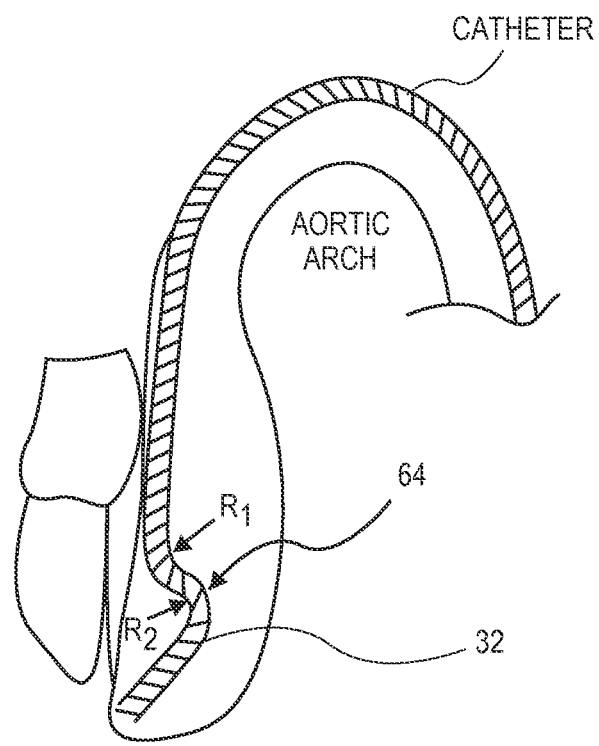
Figure 7:
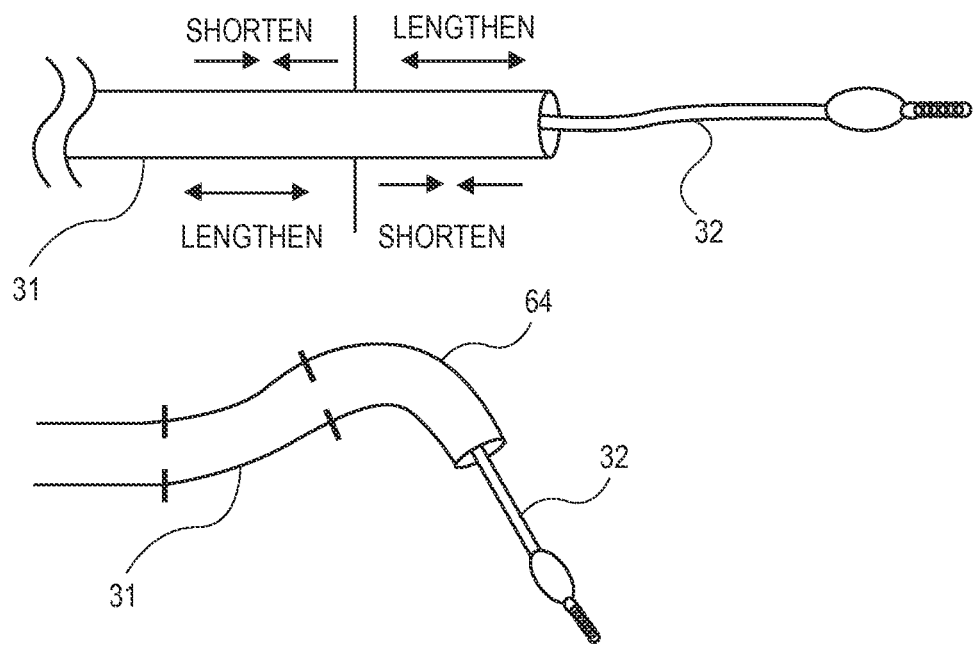
Figure 8:
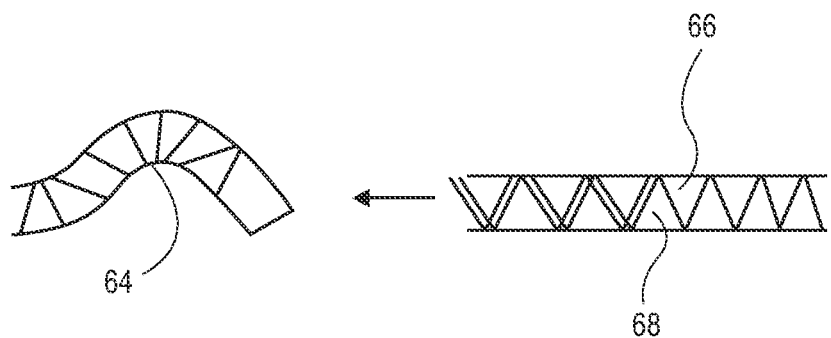

In some alternative embodiments, as shown in FIG. 6, the delivery catheter 32 is steerable. In some variations, the guide catheter is steerable (not shown). By having a steerable delivery catheter, the positioning of the partitioning device may be more controlled. For example, a steerable delivery catheter may hold the implant in place as the guide catheter is retracted to expose and/or deploy the partitioning device. The steerable delivery catheter may be steered or positioned into any number of suitable geometries. For example, the delivery catheter may be positioned into an S-curve 64. This S-curve, as shown in FIG. 6, may be configured to position the catheter away from the ventricular septum and toward the apex of the heart, for example. The delivery catheter could be steerable by one of several different mechanisms. For example, as shown in FIG. 7, pull wires (not shown) may be used to lengthen and shorten various portions of the delivery catheter 32 (within the guide catheter 31) to form the S-curve 64. As shown in FIG. 8, the delivery catheter may include interlocking shafts, such as hypotubes 66, 68. The interlocking shafts may move with respect to one another to form the S-curve 64.

In another alternative embodiment, not shown, the delivery catheter may be a shape set material, such as Nitinol. In some variations, the delivery catheter may be stiffer than the guide catheter, such that as the guide catheter is retracted or withdrawn, it imparts minimal forces on the more stiff delivery catheter. The delivery catheter may be set into any suitable shape, and be configured for any suitable vascular anatomy.

Figure 9:
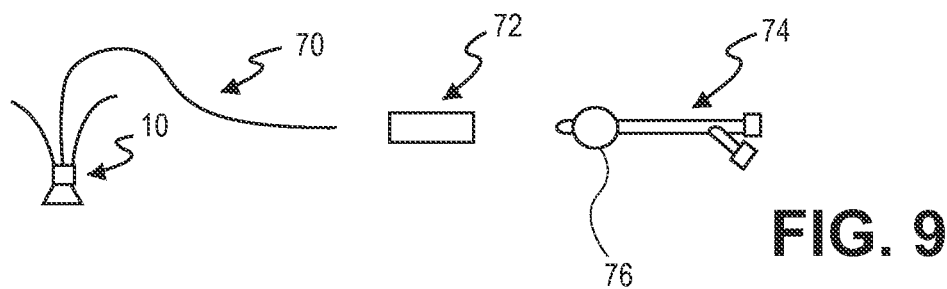
FIGS. 9-12 illustrate various embodiments of the delivery system including an "over the wire" balloon system.

In some variations, the size of the expandable member may be limited by the size of the delivery diameter. For example in the stored configuration, i.e. when the expandable member, partitioning device, and the delivery catheter are within the guide catheter, each of the components contributes to the overall delivery diameter. The delivery diameter is preferably small to enable the passing of the guide catheter through the vasculature of the patient, therefore limiting the size of the expandable member and/or the size of the delivery catheter. To address these restrictions, in some variations (e.g., FIG. 9) the components of the delivery system 30 may be decoupled or separable from each other. For example, the delivery system may be decoupled into four separate components: a partitioning device 10, a wire 70, a detachable handle 72, and an "over the wire" balloon system 74. The wire 70 may include a coupling mechanism, such as a helical screw, at the distal end that is configured to couple to the partitioning device 10. The wire may be a conventional cardiovascular wire, or any other suitable wire. The wire may have a ground profile to optimize performance. The handle 72 may be coupled to the wire during the initial placement of the device, and then may be removed to allow the balloon system 74 to be coupled to the wire and advanced toward the partition device. Coupling to the wire in this example may be defined as positioning the handle, or balloon system, over the wire such that the wire is disposed along the length of an inside diameter of the handle or system. The handle may be replaced once the balloon system is in place, or alternatively, the balloon system may include a separate handle. The balloon system 74, having expandable member 76 (a balloon), may be a conventional balloon catheter or may be any other suitable "over the wire" system that is configured to expand the partitioning device.

Figure 10:
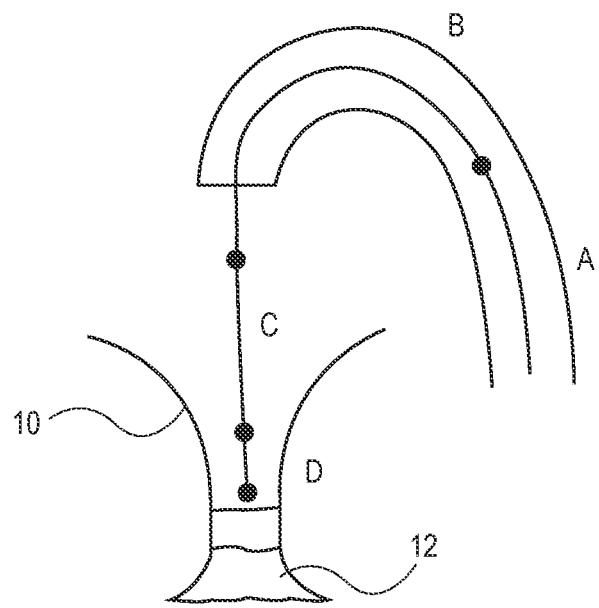
Figures 11A, 11B:
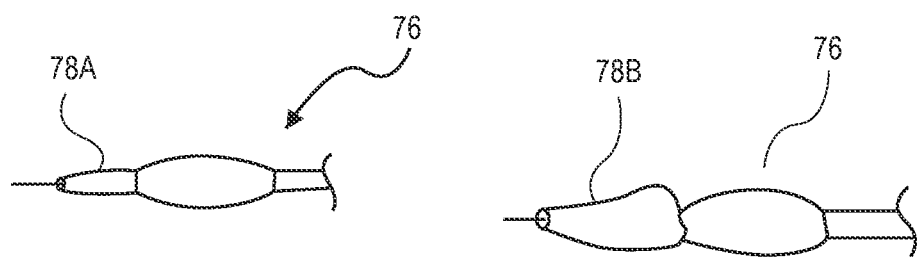

In one variation, illustrated in FIG. 10, there may be four distinct regions of the delivery system (e.g., guide catheter), each having various requirements and characteristics. For example, in FIG. 10, the guide catheter includes four regions, A-D. Region A is pushable such that it may advance the guide catheter through the vasculature of the patient and/or push the partitioning device 10 out of the guide catheter. Region A may also be torqueable depending on the configuration of the coupling mechanism, for example, if the coupling mechanism is a screw. Region A may include a hypotube or a braided or coil wound shaft. Region B may be flexible to ensure that the device is positioned correctly, and not repositioned toward the septum, for example, during deployment. As with region A, region B may also be torqueable. Region B may include a highly flexible rigid shaft such as Nitinol (or other shape memory materials) or a braided or coil wound shaft. Region C may have a low profile such that is does not largely affect the overall delivery diameter or profile. Region C may also be pushable, such that it may advance the device and/or position the hub 12 or foot of the device. Region C may be a hypotube or solid shaft. Region D may be removably attached to the partitioning device 10. Region D may include a coupling mechanism such as a coiled screw, a suture, or a hitch-pin (described below). In some variations, regions A through C may form a wire, similar to wire 70 in FIG. 9. A balloon system 74 may be advanced over regions A through C. FIGS. 11A-11B illustrate one variation of a delivery system including an expandable member that is a balloon that is deliverable over a wire forming part of the guide catheter. In this example, the balloon may be configured to minimize the overall profile of the system.

Figure 12:
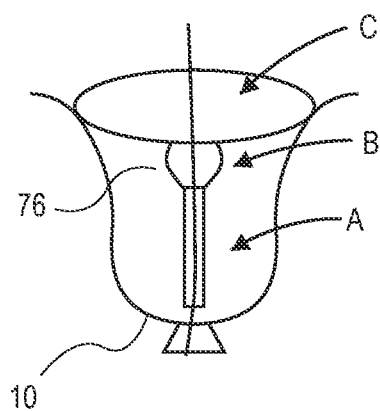
Figure 13A:
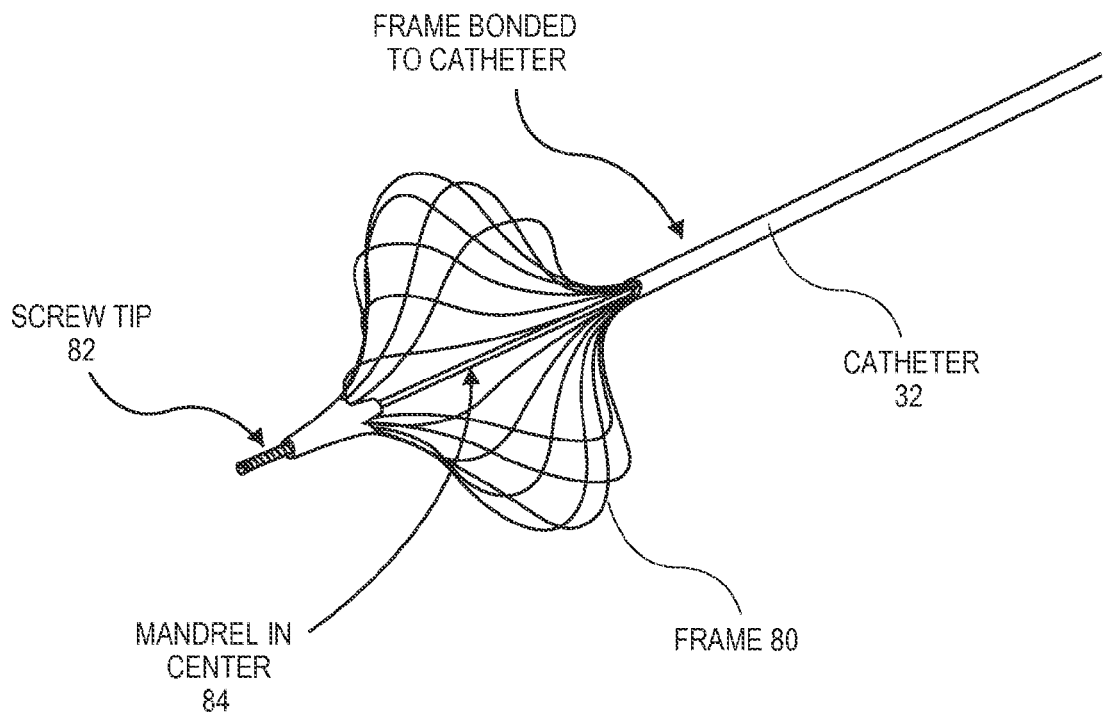
Figure 13B:
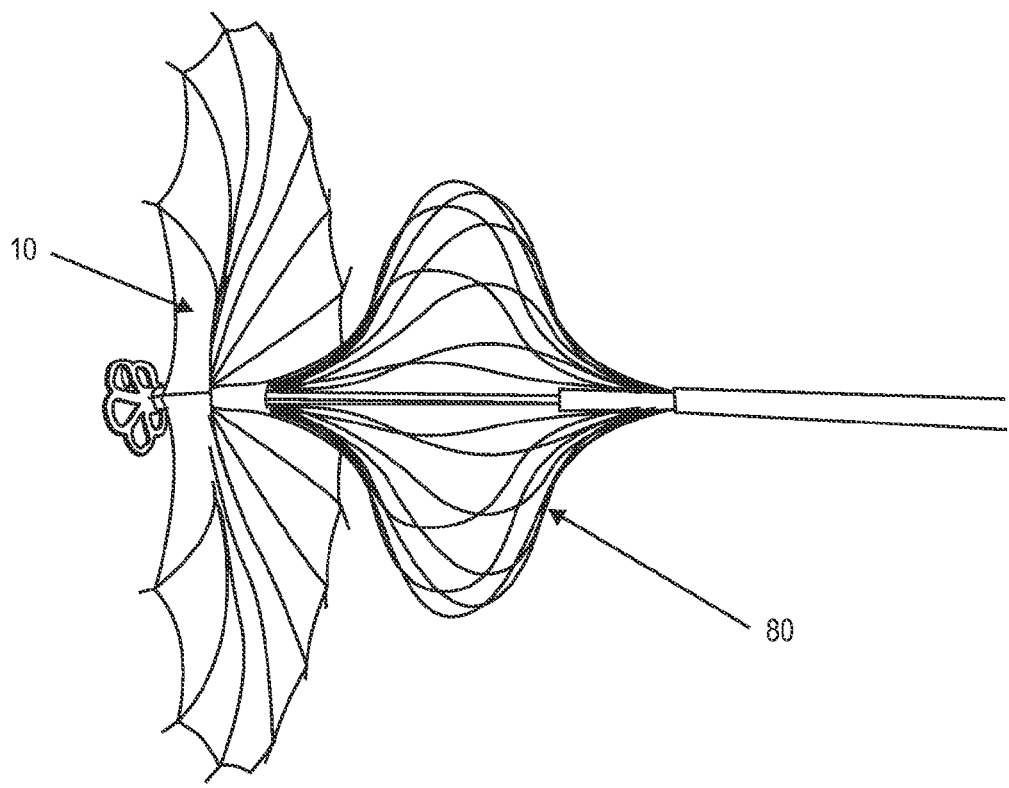
Figure 13C:
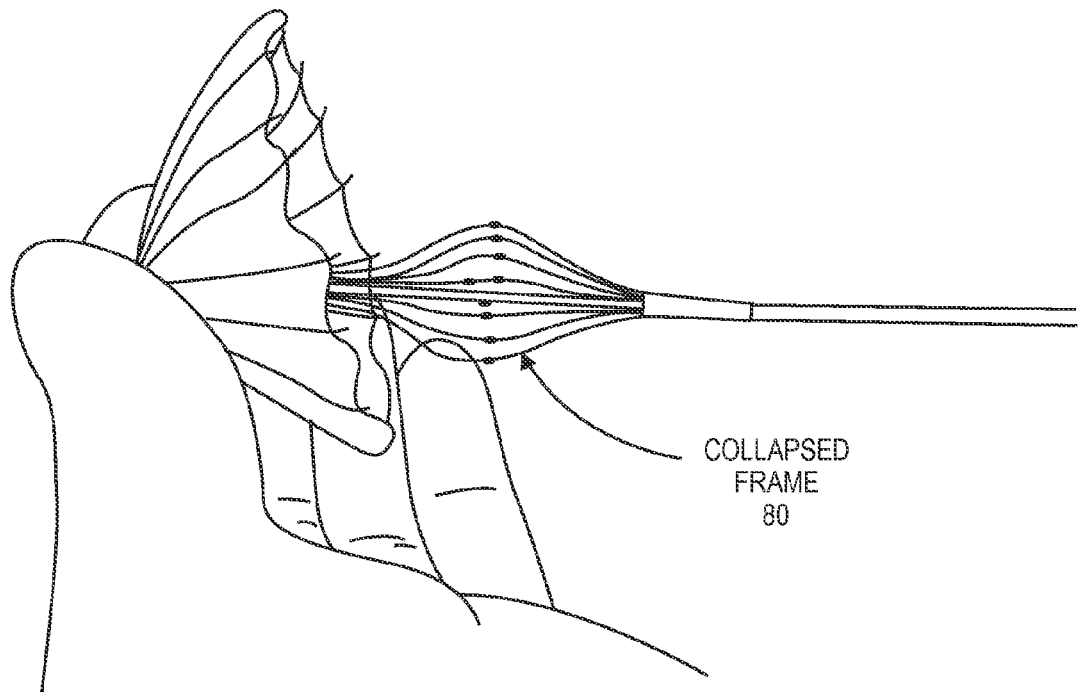
Figure 13D:
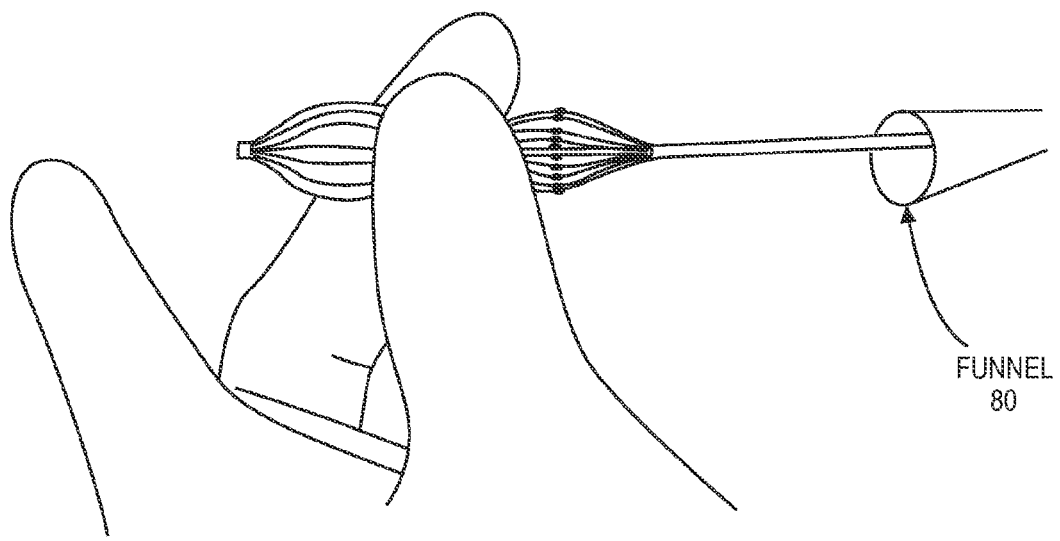
Figure 13E:
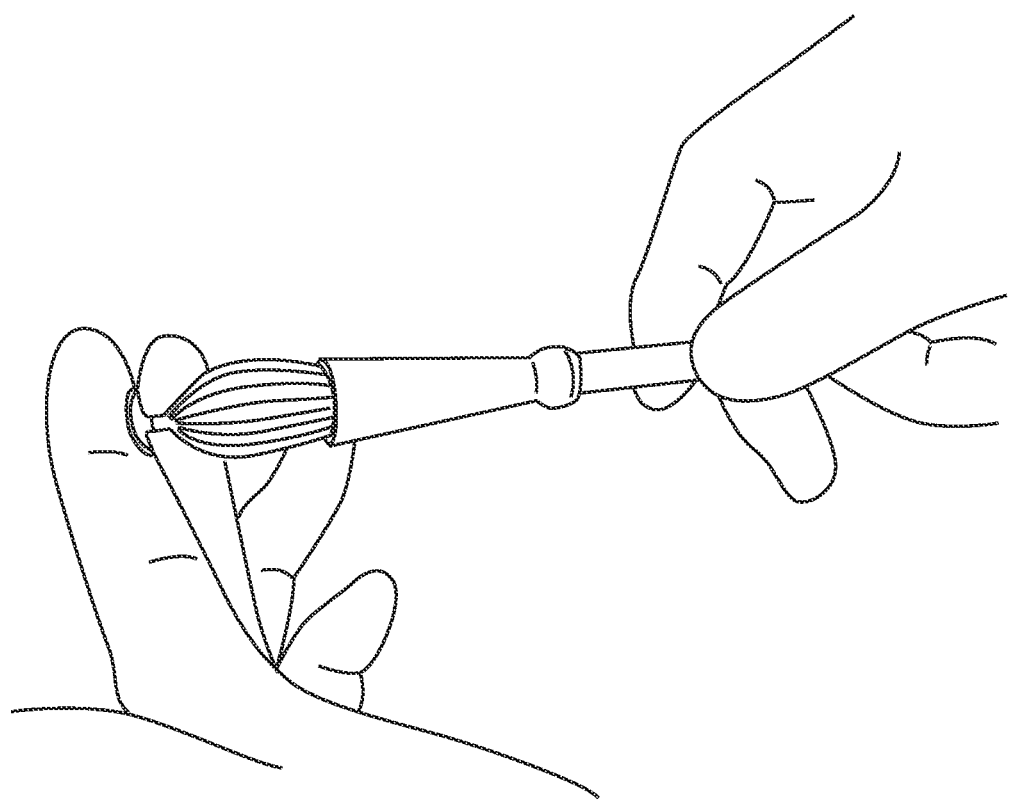
Figure 13F:
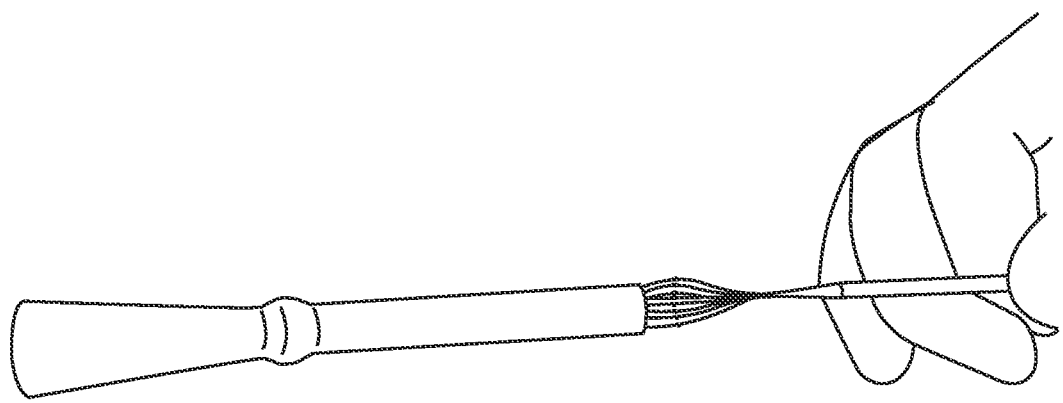

As shown in FIGS. 11A-12, balloon 76 of the balloon system 74 may include any number of features such that it is configured to expand the partitioning device 10. FIG. 11A shows a conventional angioplasty balloon tip 78A. FIG. 11B shows a more aggressive tip 78B configured to insert into the distal portion of the partitioning device 10 when it is collapsed. As shown in FIG. 12, the balloon 76 may include three portions A, B, C. In some embodiments, portion A remains within the distal end of the partitioning device 10 during delivery. The tip portion, portion A, is a distal nose region that may have a small profile such that it is configured to not largely contribute to the overall delivery profile. Portion A is also configured to position portions B and/or C in the correct position with respect to the partitioning device. For example, the length of portion A may be selected so that when balloon 76 is fully advanced, the distal tip of portion A contacts the partitioning device, and the expandable balloon (portion C) is optimally positioned to expand the partitioning device. Portion A may be part of the balloon, or it may be a separate portion such as a tube. Portion A may be stiff in some embodiments. Portion C is the expandable balloon portion and is configured to interact with the distal end of the partitioning device. Portion B may be a tapered region. The taper may be relatively gradual or more extreme, and allows the transition between the distal tip and the balloon, allowing the entire expandable region to be inserted into the collapsed partitioning device.

Another example of an expandable member is shown in FIGS. 13A-15. In this example, the expandable member is a mechanical expander. The mechanical expander in this example is a frame 80 formed of a plurality of arms or struts that are joined at their proximal and distal ends, as shown. The arms may be collapsed down or expanded by moving the proximal and distal ends of the frame relative to one another. The proximal end of the frame 80 may be coupled to the delivery catheter 32 and the distal end of the frame may include a coupling mechanism 82, such as a screw tip. The coupling mechanism may be coupled to the partitioning device 10, as shown in FIG. 13B. The frame 80 may further include a mandrel 84 configured to move the frame 80 from a collapsed to an expanded configuration. A pull wire or other suitable mechanism may be coupled to the mandrel 84 such that it may be moved and thereby move the frame 80. FIGS. 13C to 13F illustrate loading the implant (partitioning device) onto a guide catheter such as the one shown in FIGS. 13A-13B. The implant may be coupled to the guide catheter in an expanded state, and then collapsed down (around the mechanical expander as shown in FIG. 13D). A loading tool (e.g., funnel) device may be used to help load the implant onto the delivery system, as shown in FIGS. 13E and 13F. Once the implant is in the loading tool the system may be loaded into a delivery catheter for inserting into the patient. The implant may be flushed (e.g., with saline) first.

Figure 14:
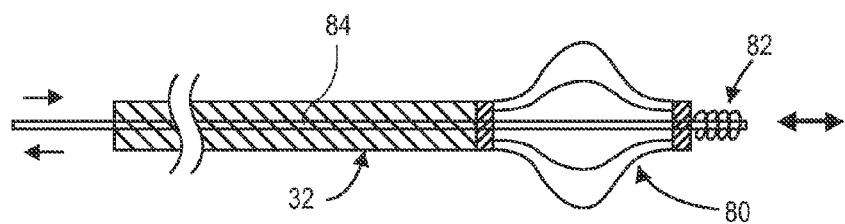
Figure 15:
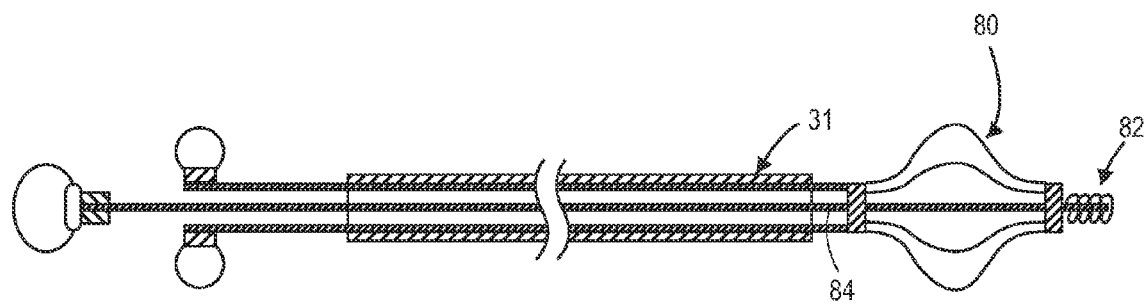

FIGS. 14 and 15 illustrate another variation of a delivery catheter including a mechanical expander. In this variation, the expander region is controlled by a mandrel 84 that is extendable and retractable to collapse or expand the mechanical expander region. FIG. 15 shows one variation in which a proximal handle includes grips (finger grips) for actuating the expander relative to the rest of the catheter. Expanding the mechanical expander pushes against the inner portion of a collapsed implant and aids it in expansion and attachment (sealing) to the ventricle wall(s). The mechanical expanders described herein may have advantages compared to the balloon expanders mentioned above. For example, the mechanical expanders may be precisely controlled. In addition, the mechanical expander may be shaped to more optimally contact the implant. Finally, the mechanical expander may be expanded larger than the balloons, while having a smaller cross-sectional area, thereby allowing smaller diameter delivery/guide catheters. In addition, the mechanical expander may not require the pressurized inflation fluid.

Figure 16:
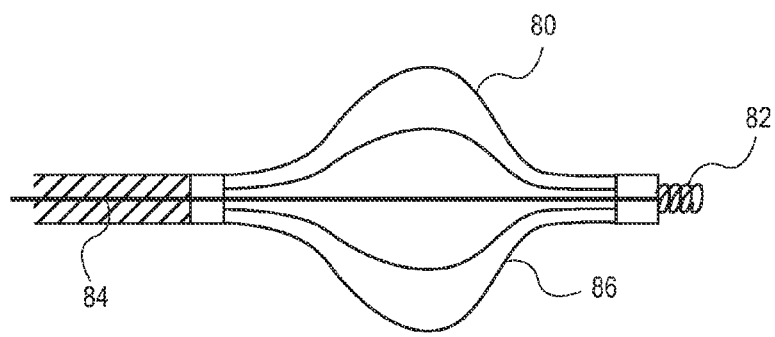
Figure 17:
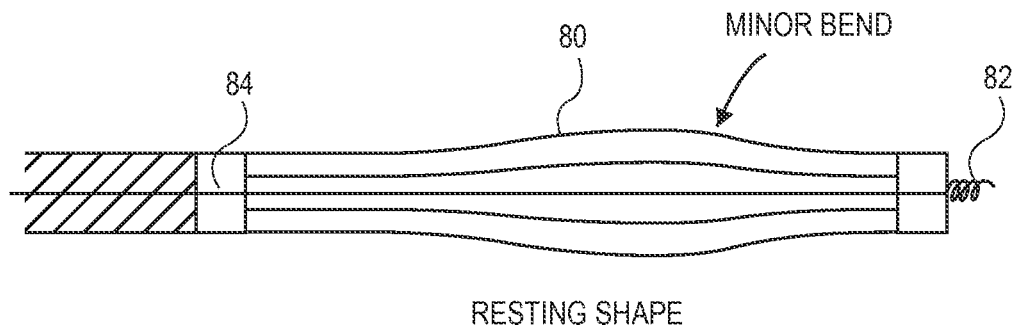
Figure 18:
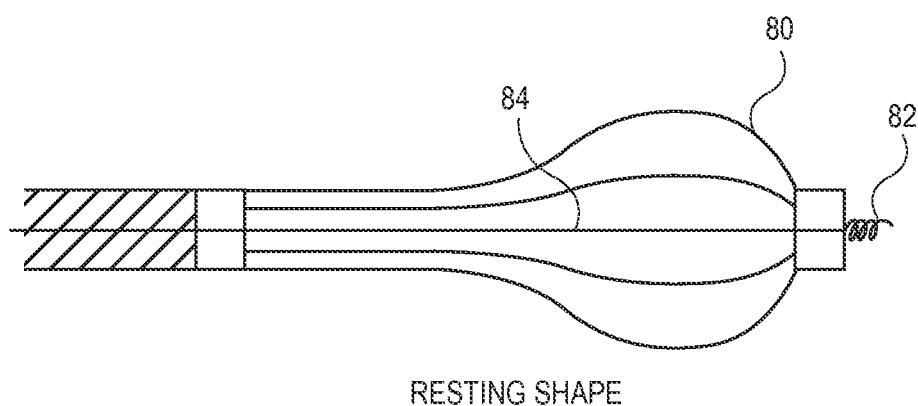
Figure 19:
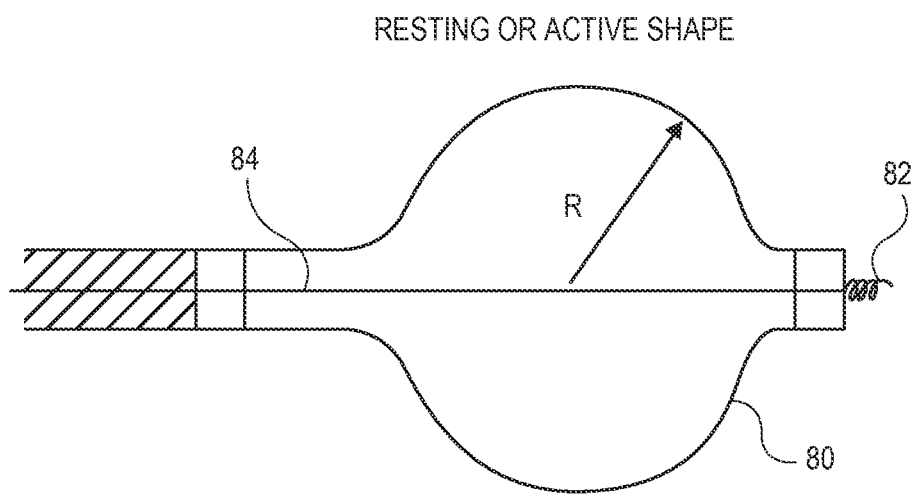

FIGS. 16-21 illustrate variations of mechanical expanders. For example, as shown in FIG. 16, the frame 80 may be formed of heat set Nitinol, or other shape memory material, in a shape such that the resting position is the expanded position, as shown. The frame may be made out of a tube that is laser cut to form the struts 86 of the frame 80. In this configuration, the mandrel 84 may be pushed to compress the frame radially such that it may be advanced through the guide catheter. The mandrel 84 may then be pulled to expand the struts 86 radially to expand the frame 80. As shown in FIG. 17, the frame 80 may be collapsed by pulling end proximal and distal ends apart. As mentioned, the frame (arms/struts) may be made at least in part from heat set Nitinol, or other shape memory material, in an expanded or unexpanded shape. The frame may be made out of a tube that is laser cut to form the struts 86 of the frame 80. In this configuration, the mandrel 84 may be pushed to compress the frame radially such that it may be advanced through the guide catheter. The mandrel 84 may then be pulled to expand the struts 86 radially to expand the frame 80. The material of the frame 80, such as Nitinol, may be heat treated such that the struts are predisposed to expand. As shown in FIG. 18, the frame 80 may have a symmetric or asymmetric shape along its axial length. For example, in FIG. 18, the frame is a teardrop shape. In some variations the wider diameter region of the tear drop shape is located more proximally, nearer the region where the implant will expand the most (and contact the wall of a ventricle). The material of the frame 80, such as Nitinol, may be heat treated such that the struts are predisposed to expand at the distal or proximal end of the frame. In this embodiment, the frame may contact the device 10 further down on the device, requiring less radial expansion to open the implant. As shown in FIG. 19, the frame 80 may expand into a fully circular shape. As shown in FIG. 20, the frame 80 may be made out of a spiral cut tube. The material of the frame 80, such as Nitinol, may be heat treated such that the struts are predisposed to expand. This configuration is such that at least a portion of the frame 80 will contact the device 10 on the ribs 14 of the device, since the spiral of the expansion member frame will place the frame arms at an angle relative to the ribs of the implant. Thus the frame may push against the ribs of the implant preferentially, rather than the membrane. FIG. 21 illustrates an example in which the arms forming the frame are cut to bias the bending (hinge) region. In this example, cuts 88 in the frame material are configured to predispose bending of the frame at specified locations. A detailed view is shown in FIG. 21A. The cuts 88 may be placed in any suitable location for any suitable device geometry.

As shown in FIGS. 22-23B, the mechanical expansion member (e.g., frame 80) and the catheter 32 (e.g., guide catheter) may be made out of a single length of tube. In the example shown in FIG. 22, the distal end region of the tube includes keyed slots 90 cut into the tube to form a flexible portion of the delivery catheter 32. Toward the more distal end of the tube, slots 92 have been cut into the tube to form the expandable struts 86 of frame 80. In some variations the keyed slots 90 may be formed by a single, continuous helical cut. Alternatively, keyed slots may be formed by multiple circumferential cuts along the length of the delivery catheter portion. The catheter 32 in this embodiment may be more flexible than a standard hypotube, while still being torqueable and having a good push/pull response. FIGS. 23A and 23B illustrate partial views of "unrolled" templates for some of the laser cuts that may be made to form a catheter having a mechanical expansion member. For example, FIG. 23A shows a version with laser cut arms that run parallel to the long axis of the catheter, while FIG. 23B shows a variation in which the laser cut arms spiral around the circumference of the catheter once it has been constructed.

Figure 24:
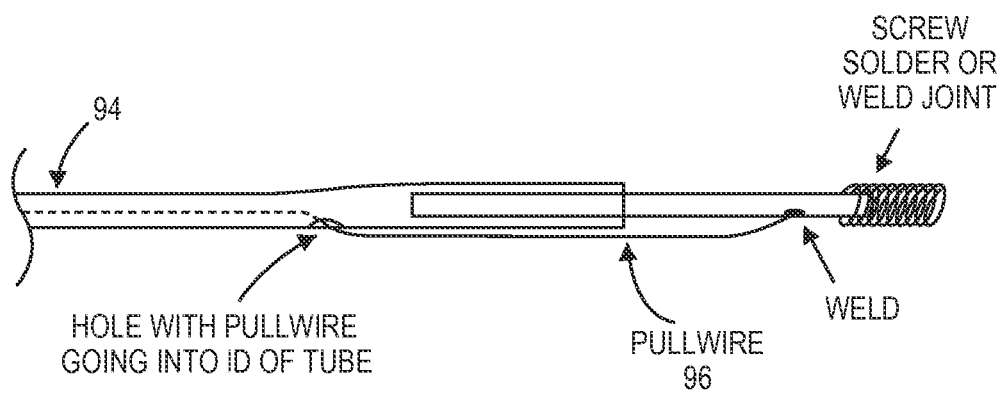
Figure 25:
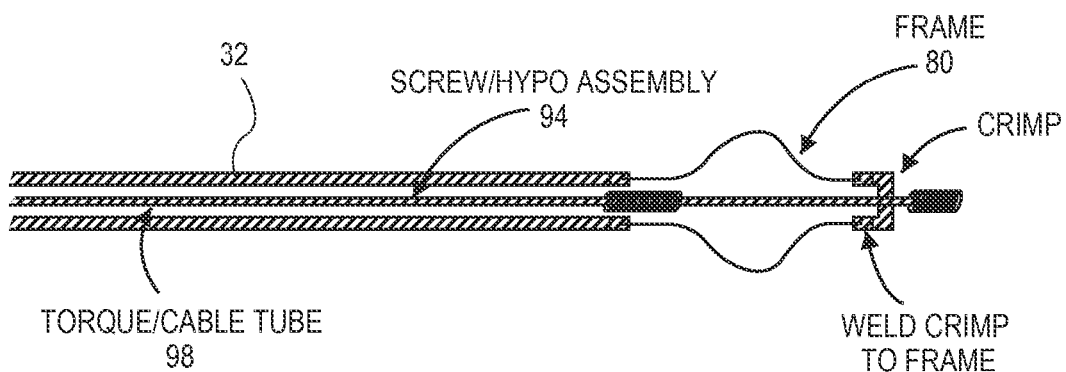
FIG. 25 illustrate an alternative embodiment of a delivery system wherein the frame and catheter are formed from separate components.

As shown in FIG. 22, the delivery system may further include a tube and/or shaft 94 within the catheter. FIG. 24 shows a more detailed example of this tube. A Tube/shaft 94 may be configured to couple to the coupling mechanism 82 (or to be part of the coupling mechanism) to release the device 10. The tube/shaft 94 may move independently from the rest of the catheter 32, and may be referred to as a torque shaft. Alternatively or additionally, the tube/shaft 94 may include a lumen through which any suitable liquid may be injected. As shown in FIG. 24, the system may further include a pull wire 96. In this example, the pull wire may function to pull and/or deflect the distal end of the catheter to steer and position the partitioning device. As shown, the pull wire does not have to go through torque tube 94, but could run along the outside of the tube and/or delivery catheter 32. FIG. 25 shows one variation of a guide catheter including an extruded plastic cover 98 over a portion of the guide catheter. In another variation, the catheter is plastic, and the mechanical expansion members are secured thereto. In some embodiments, a reflow process may be utilized to bond the plastic onto the torque tube.

Figure 26:
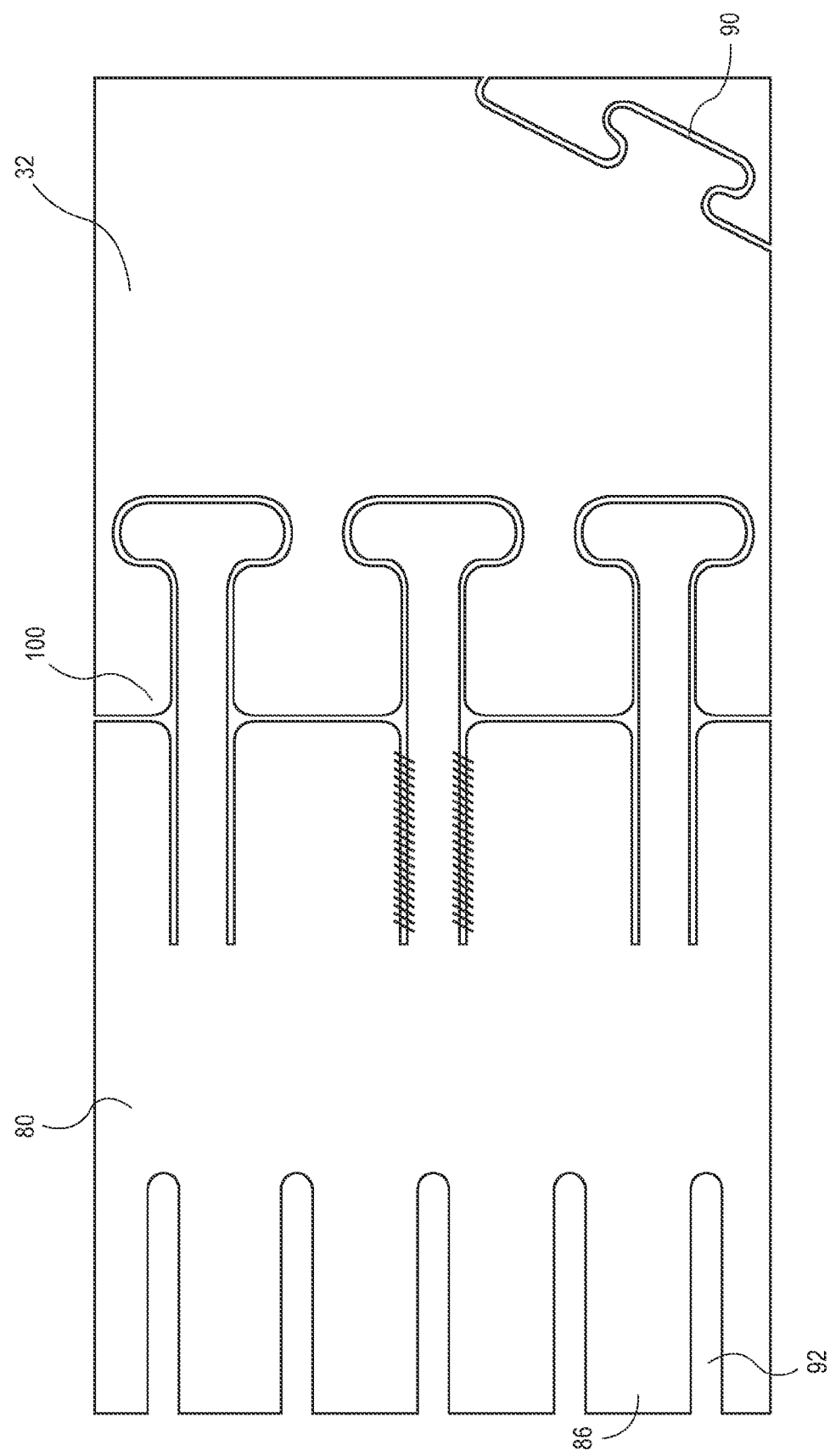
FIG. 26 illustrates an alternative embodiment of the delivery system wherein the frame and the guide catheter are formed from tubes and snapped together.

In general, it may be beneficial to have the mechanical expansion member be formed of a shape memory or hyperelastic material such as Nitinol. However, it may be desirable to have the rest of the catheter (e.g., the rest of the body region proximal to the expansion member) formed of a different material, such as stainless steel. FIG. 26 illustrates one variation of a catheter (or region of a catheter) having a Nitinol mechanical expansion region and a stainless steel proximal region. In FIG. 26, rather than forming the guide catheter 32 and the frame 80 out of a single tube, the catheter may be formed out of a first tube of a first material (e.g., stainless steel), and the frame 80 forming the arms of the mechanical expansion member may be formed out of a second material (e.g., Nitinol). This configuration may allow the delivery system to be made in a more cost effective manner. As shown in FIG. 26, the proximal end of the frame 80 and the distal end of the delivery catheter may include cuts 100 that are configured to snap the proximal end of the frame 80 onto the distal end of the delivery catheter. Cuts 100 provide a good mechanical interface between the frame 80 and the delivery catheter 32, providing enhanced column strength beyond what a simple weld may produce. Cuts 100 may also allow the tabs to bend and the tubes to be joined. After snapping the tubes together, cuts 100 are welded closed, eliminating the flexibility of the tabs thereby locking the tubes together (without requiring dissimilar metals to be welded, which may cause faults in the final product).

In some variations the expandable member is a pneumatic, or fluid-pressure based member, as shown in FIGS. 27A and 27B. In this example, the expandable member may include a hydraulic system that is configured to apply pressure to the inner surface 18 of the partitioning device 10 to drive it open and/or seal it to the ventricle wall. The system may use a rapid saline injection or any other suitable system to apply pressurized fluid flow against the inner surface 18 of the partitioning device 10 to expand the device 10. In some variations, the system may inject a contrast to aid in the radiopacity of the device and/or area surrounding the device. The expansion member may include a fluid delivery member (tube, passage, etc.) that has multiple ports oriented at different directions/angles to drive the fluid against the partitioning device to deploy the partitioning device.

Figure 28A:
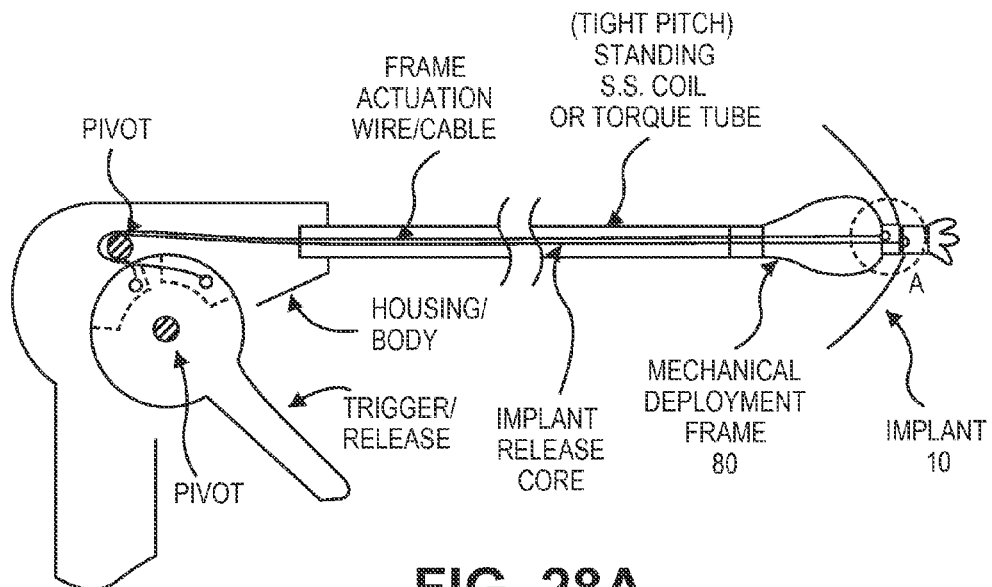
FIGS. 28A-32 illustrate several variations of deployment systems, i.e. handles.
Figure 28B:
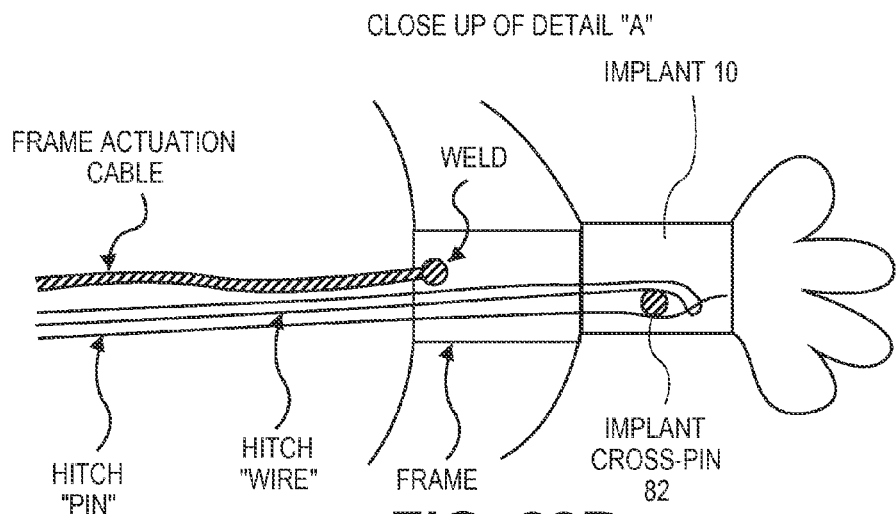

In general, after a partitioning device 10 has been properly positioned within the ventricle, the partitioning device 10 may be deployed and/or released from the guide catheter. As shown in FIGS. 28A-32, the delivery system may include one of several variations of deployment systems, i.e. handles. The deployment of the device is preferably performed in a controlled manner. As shown in FIGS. 28A-28B, the system may include a "pistol grip" handle. This embodiment may include any of the following features: one handed actuation/deployment and release of the partitioning device 10, a keyed interaction between the handle and the catheter to allow for rotation of the partitioning device prior to release, a torsion spring to allow for multiple expansions of the deployment frame 80 prior to release of the partitioning device, a hitch-pin coupling mechanism 82 as described in more detail below, and a pre-loaded partitioning device within the delivery system.

Figure 29:
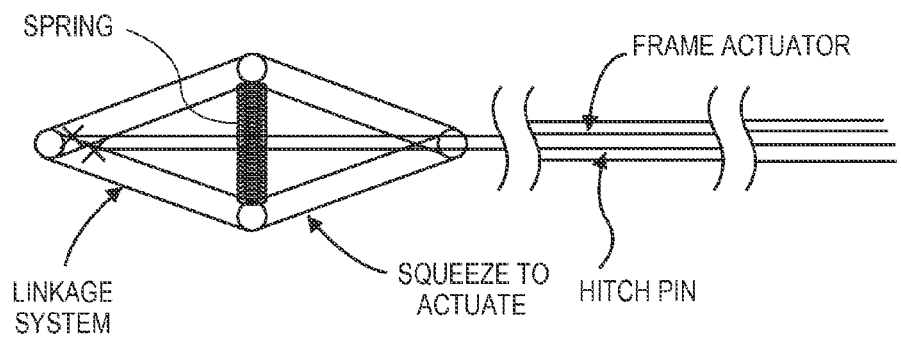
Figure 30:
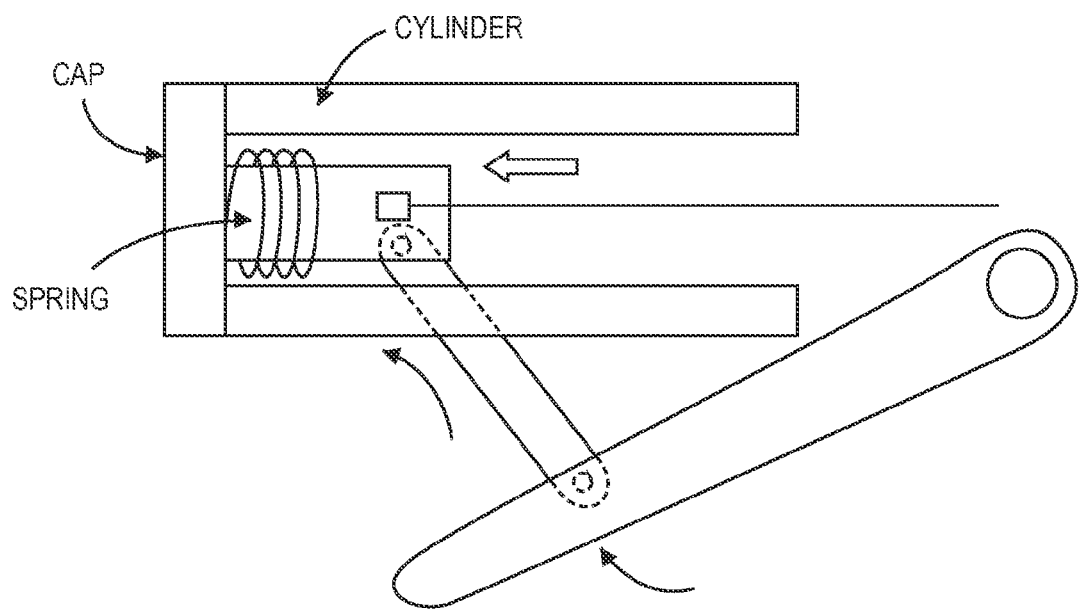
Figure 31:
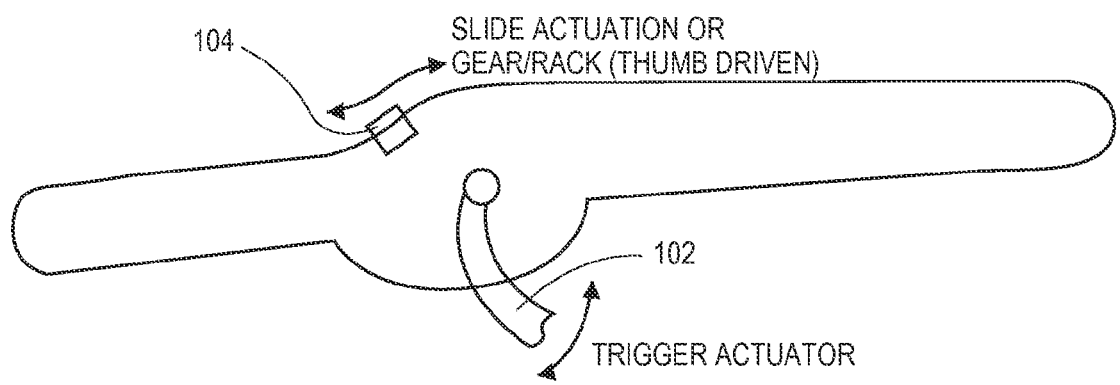
Figure 32:
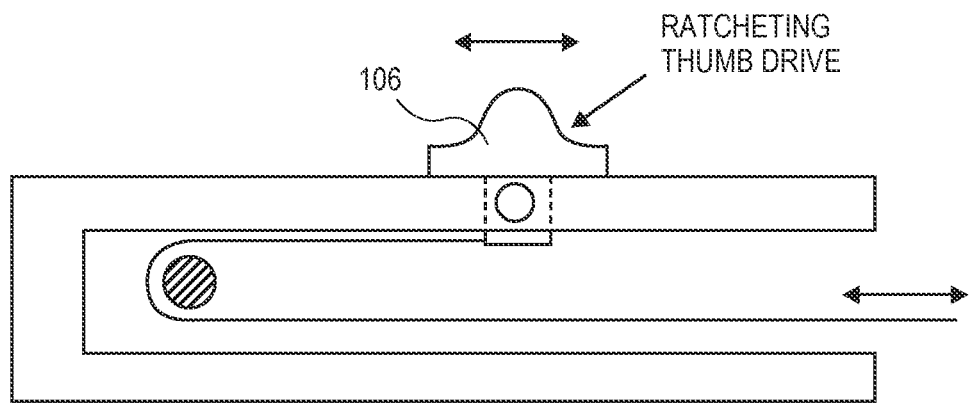

In one variation, shown in FIG. 29, the system may include a "squeeze grip" handle. This handle may also include any combination of the features listed above. FIG. 30 shows another variation of a "squeeze grip" handle, having a trigger-like control for driving contraction/extension of a pullwire, which may be connected to a mechanical expansion member and/or a coupling element. As shown in FIG. 31, the system may include a "remote grip" handle. This handle may be actuated by a mechanism such as a trigger 102, a slide 104, and/or a button. As shown in FIG. 32, the system may include a "sliding grip" handle. This handle may be actuated by a mechanism such as a ratcheting thumb button 106. Any of the handles described herein may be used as part of an expansion control and/or a deployment control.

Figure 33:
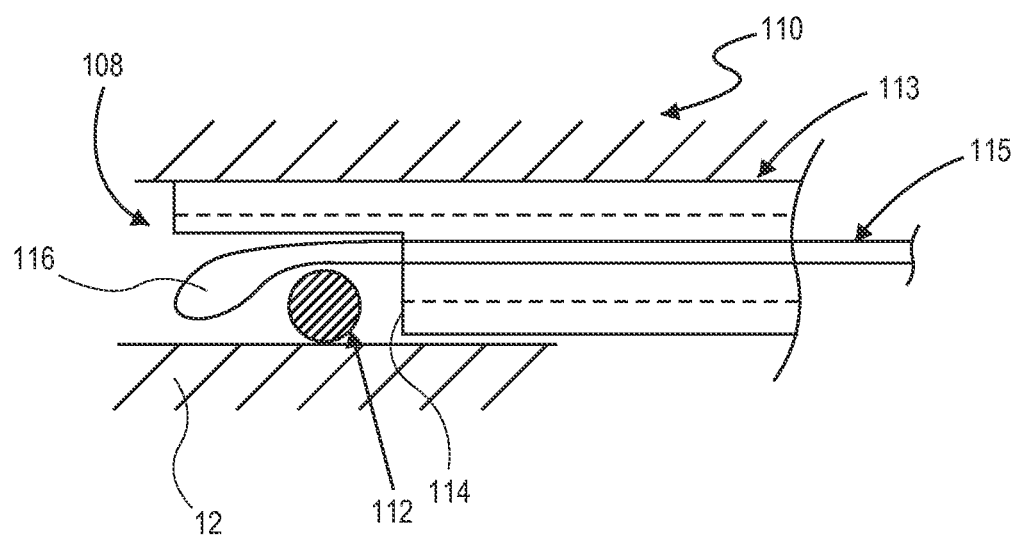
FIG. 33 illustrates an alternative embodiment of the coupling mechanism.

The partitioning device may be coupled to the delivery catheter and then released in one of several embodiments. In some embodiments, a torque shaft within the delivery system is rotated to disengage the helical coil screw 53 of the delivery catheter 32 from the hub 12. The rotation of the torque shaft 48 rotates the helical coil screw 53 which rides on the connector bar 20 secured within the hub 12. Once the helical coil screw 53 disengages the connector bar 20, the delivery system 30, including the guide catheter 31 and the delivery catheter 32, may then be removed from the patient. In alternative embodiments, as shown in FIG. 33, the coupling mechanism is a hitch-pin mechanism 108. The hitch-pin 108 may include several components. For example, the hitch pin may include a feature 110 in the device foot 12 allowing for entry of the retention/release mechanism. Further, the hitch pin includes a feature 112 within feature 110 that is configured to partially restrict the hole (feature 110). In some variations, feature 112, is a cross pin. Feature 113 may be a tube with a notch 114 in the distal end of the tube. Feature 115 may be a rod with a bulbous feature 116 on the distal end of the rod. With tube 113 in place, the bulbous feature 116 cannot fit past cross pin 112, however, once feature 113 is removed, the rod 115 and end 116 can be removed. Tube 113 is removed by pulling the tube in the proximal direction. This motion may be simpler than a torque motion required to decouple the helical screw embodiment.

As shown in FIG. 3E, the partitioning component 10 partitions the patient's heart chamber 57 into a main productive or operational portion 58 and a secondary, essentially non-productive portion 59. In some embodiments, the operational portion 58 is much smaller than the original ventricular chamber 57 and provides for an improved ejection fraction. The partitioning increases the ejection fraction and provides an improvement in blood flow.

In some embodiments, it may be desirable to select a partitioning device that is most suitably sized and configured for a specific patient. This may be done in one of several different variations. In some embodiments, the patient may be pre-measured to determine a suitable device size. The patient may be measured in one of many suitable ways, including, but not limited to, mechanical or hydraulic measurement, 3D echo, CAT scan or LV-gram.

In some embodiments, a method for placement of the device through a jugular vessel may include the following steps: local anesthesia, insert a guidewire into a jugular vessel, advance the guidewire across the ventricular septum, advance the delivery system (and partitioning device) over the wire and into location, drive the distal tip and partitioning device toward the apex of the heart, deploy the implant, withdraw the guide and delivery catheters. In some embodiments, a method for placement of the device through a femoral vessel may include the following steps: local anesthesia, insert a guidewire into a femoral vessel—may use a LV gram for proper positioning, advance the guidewire across the ventricular septum, advance the delivery system and partitioning device (in some cases without a guide catheter) over the wire crossing the valve and into location, drive the distal tip and partitioning device toward the apex of the heart, deploy the implant, withdraw the guide and delivery catheters.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

What is claimed is:

1. A delivery system for delivering a ventricular partitioning device into a patient's ventricle and deploying the partitioning device to reduce the effective volume of the ventricle by expanding the partitioning device from a collapsed delivery configuration into an expanded deployed configuration, the system comprising:
  an elongate delivery catheter having a proximal end and a distal end;
  an expansion member near the distal end of the delivery catheter and configured to expand a plurality of struts extending from a central hub located at a distal end of the partitioning device by applying pressure to the collapsed partitioning device to open the partitioning device and secure it in the ventricle; and
  a coupling element configured to removably secure to the hub of the partitioning device to retain the expansion member at least partially surrounded by the collapsed partitioning device prior to deployment.

2. The system of claim 1 further comprising an expansion control for expanding the expansion member to apply pressure and expand the ventricular partitioning device.

3. The system of claim 2, wherein the expansion control comprises an inflation lumen connected to the expansion member.

4. The system of claim 2, wherein the expansion control comprises a pullwire for pulling on the expansion member to expand it.

5. The system of claim 2, wherein the expansion control comprises a button, knob, slider, or dial on the proximal end of the elongate delivery catheter for controlling expansion of the expansion member.

6. The system of claim 1 further comprising a deployment control for releasing the coupling element from the hub of the ventricular partitioning device.

7. The system of claim 6, wherein the deployment control comprises a torque shaft connected to the coupling element for unscrewing the coupling element from the ventricular partitioning device.

8. The system of claim 6, wherein the deployment control comprises a pullwire connected to the coupling element for pulling a hitch pin to release the ventricular partitioning device.

9. The system of claim 1 further comprising a ventricular partitioning device wherein the ventricular partitioning device comprises an umbrella-like structure having a plurality of struts joined at a central hub.

10. The system of claim 1, wherein the expansion member is a hydraulic expansion member comprising a plurality of openings for releasing pressurized fluid to apply pressure to expand the ventricular partitioning device.

11. The system of claim 1, wherein the expansion member is an inflatable balloon.

12. The system of claim 1, wherein the expansion member is a mechanical expander comprising a plurality of struts joined at their proximal and distal ends and configured to expand outwards when the proximal and distal ends are brought closer together.

13. The system of claim 1, wherein the coupling element comprises a helical screw.

14. The system of claim 1, wherein the coupling element comprises a hitch pin.

15. The system of claim 1, wherein the delivery catheter further comprises a proximal handle having a one-handed activation release.

16. The system of claim 1 further comprising a steering mechanism that bends the distal end region of the delivery catheter.

17. The system of claim 1, wherein the coupling element is distal to the expansion member.

18. The system of claim 17, wherein the coupling element is entirely distal to the expansion member.

19. A delivery system for delivering a ventricular partitioning device into a patient's ventricle and deploying the partitioning device to reduce the effective volume of the ventricle by expanding the partitioning device from a collapsed delivery configuration into an expanded deployed configuration, the system comprising:
  an elongate delivery catheter having a proximal end and a distal end;
  an expansion member near the distal end of the delivery catheter and configured to expand the partitioning device by applying pressure to open the collapsed partitioning device and secure it in the ventricle;
  a coupling element configured to deployably secure to a hub of the partitioning device to retain the expansion member at least partially surrounded by the collapsed partitioning device prior to deployment, the hub located on a distal end of the partitioning device;
  an expansion control at the proximal end of the elongate delivery catheter for expanding the expansion member to apply pressure and expand the partitioning device; and
  a deployment control for releasing the partitioning device from the delivery catheter by separating the coupling element from the hub of the partitioning device.

20. The system of claim 19, wherein the expansion control comprises an inflation lumen connected to the expansion member.

21. The system of claim 19, wherein the expansion control comprises a pullwire for pulling on the expansion member to expand it.

22. The system of claim 19, wherein the expansion control comprises a button, knob, slider, or dial on the proximal end of the elongate delivery catheter for controlling expansion of the expansion member.

23. The system of claim 19, wherein the deployment control comprises a torque shaft connected to the coupling element for unscrewing the coupling element from the ventricular partitioning device.

24. The system of claim 19, wherein the deployment control comprises a pullwire connected to the coupling element for pulling a hitch pin to release the ventricular partitioning device.

25. The system of claim 19 further comprising a ventricular partitioning device wherein the ventricular partitioning device comprises an umbrella-like structure having a plurality of struts joined at a central hub.

26. The system of claim 19, wherein expansion member is a hydraulic expansion member comprising a plurality of openings for releasing pressurized fluid to apply pressure to expand the ventricular partitioning device.

27. The system of claim 19, wherein the expansion member is an inflatable balloon.

28. The system of claim 19, wherein the expansion member is a mechanical expander comprising a plurality of struts joined at their proximal and distal ends and configured to expand outwards when the proximal and distal ends are brought closer together.

29. The system of claim 19, wherein the coupling element comprises a helical screw.

30. The system of claim 19, wherein the coupling element comprises a hitch pin.

31. The system of claim 19, wherein the delivery catheter further comprises a proximal handle having a one-handed activation release.

32. The system of claim 19 further comprising a steering mechanism that bends the distal end region of the delivery catheter.

33. A delivery system for delivering an umbrella-shaped ventricular partitioning device into a patient's ventricle and mechanically deploying the partitioning device to reduce the effective volume of the ventricle by expanding the partitioning device from a collapsed configuration into an expanded configuration, the system comprising:
- an elongate delivery catheter having a proximal end and a distal end;
- a mechanical expander near the distal end of the delivery catheter having a plurality of discrete arms configured to extend outwards when operated to apply pressure to the partitioning device to open the partitioning device; and
- a coupling element distal to the expansion member and configured to removably secure to a central hub of the partitioning device and to retain the expansion member at least partially surrounded by the collapsed partitioning device prior to deployment.

34. A delivery system for delivering an umbrella-shaped ventricular partitioning device into a patient's ventricle and deploying the partitioning device to reduce the effective volume of the ventricle by expanding the partitioning device from a collapsed configuration into an expanded configuration, the system comprising:
- an elongate delivery catheter having a proximal end and a distal end;
- a mechanical expander near the distal end of the delivery catheter comprising a plurality of discrete arms joined at their proximal and distal ends and configured to expand outwards when the proximal and distal ends are brought closer together, the mechanical expander configured to apply pressure the partitioning device to open the partitioning device and secure it in the ventricle; and
- a coupling element distal to the expansion member and configured to removably secure to a hub of the partitioning device and to retain the expansion member at least partially surrounded by the collapsed partitioning device prior to deployment.

35. A delivery system for delivering an umbrella-shaped ventricular partitioning device into a patient's ventricle and deploying the partitioning device to reduce the effective volume of the ventricle by expanding the partitioning device from a collapsed configuration into an expanded configuration, the system comprising:
- an elongate delivery catheter having a proximal end and a distal end;
- an inflatable expander near the distal end of the delivery catheter configured to extend outwards when inflated to apply pressure to open the partitioning device and to secure the partitioning device in the ventricle, wherein the inflatable expander has a proximal end that is distal the proximal end of the partitioning device in the collapsed delivery configuration; and
- a coupling element configured to removably secure to a central hub of the partitioning device and to retain the inflatable expander at least partially surrounded by the partitioning device prior to deployment, the central hub located on a distal end of the partitioning device.

36. The system of claim 35, further comprising:
- a distal nose spacer distal to the inflatable expander and proximal the central hub region on the delivery catheter and configured to space the inflatable expander proximally from the central hub region of the partitioning device.

37. The system of claim 36, further comprising a taper region between the distal nose spacer and the inflatable expander.

38. A delivery system for delivering an umbrella-shaped ventricular partitioning device into a patient's ventricle and mechanically deploying the partitioning device to reduce the effective volume of the ventricle by expanding the partitioning device from a collapsed configuration into an expanded configuration, the system comprising:
- an elongate delivery catheter having a proximal end and a distal end;
- a pressure expander near the distal end of the delivery catheter comprising a plurality of openings from a fluid source line extending along the length of the elongate catheter, the plurality of openings positioned near the distal end of the elongate delivery catheter and configured to release fluid that directly contacts and applies pressure to the proximal end region of the partitioning device to expand the partitioning device; and
- a coupling element distal to the expansion member and configured to removably secure to a central hub of the partitioning device and to retain the expansion member at least partially surrounded by the partitioning device prior to deployment.

* * * * *